(12) United States Patent
Edwards et al.

(10) Patent No.: US 6,660,529 B2
(45) Date of Patent: Dec. 9, 2003

(54) HETEROARYL SUBSTITUTED BENZOTHIAZOLE DIOXETANES

(75) Inventors: Brooks Edwards, Cambridge, MA (US); Irena Bronstein, Newton, MA (US); Zhixian Wang, Winchester, MA (US)

(73) Assignee: PE Corporation, Bedford, MA (US)

( * ) Notice: Subject to any disclaimer, the term of this patent is extended or adjusted under 35 U.S.C. 154(b) by 87 days.

(21) Appl. No.: 09/945,652

(22) Filed: Sep. 5, 2001

(65) Prior Publication Data
US 2002/0055181 A1 May 9, 2002

Related U.S. Application Data

(63) Continuation-in-part of application No. 09/362,047, filed on Jul. 28, 1999, now Pat. No. 6,355,441.
(60) Provisional application No. 60/094,336, filed on Jul. 28, 1998.

(51) Int. Cl.[7] .................... G01N 21/76; G01N 33/532; G01N 33/573; C07D 417/04
(52) U.S. Cl. .................... 436/172; 435/7.4; 435/7.9; 436/544; 544/333; 546/167; 546/270.1; 548/152; 548/156; 548/159
(58) Field of Search ............... 546/270.1, 167; 544/333; 548/152, 156, 159; 436/544, 172; 435/7.4, 7.9

(56) References Cited

U.S. PATENT DOCUMENTS

| | | | |
|---|---|---|---|
| 4,978,614 A | 12/1990 | Bronstein | |
| 5,013,827 A | 5/1991 | Schaap | |
| 5,326,882 A | 7/1994 | Bronstein et al. | |
| 5,591,591 A | 1/1997 | Bronstein et al. | |
| 5,652,345 A | 7/1997 | Schaap et al. | |
| 5,679,802 A | 10/1997 | Bronstein et al. | |
| 5,753,436 A | 5/1998 | Bronstein et al. | |
| 5,763,681 A | 6/1998 | Edwards et al. | |
| 5,840,919 A | 11/1998 | Bronstein et al. | |
| 5,843,681 A | 12/1998 | Bronstein et al. | |
| 5,981,768 A | 11/1999 | Bronstein et al. | |
| 6,124,478 A | 9/2000 | Bronstein et al. | |
| 6,218,135 B1 | 4/2001 | Matsumoto et al. | |
| 6,355,441 B1 * | 3/2002 | Edwards et al. | |

FOREIGN PATENT DOCUMENTS

| | | |
|---|---|---|
| EP | 0348491 | 8/1994 |
| EP | 0387342 | 8/1995 |
| EP | 0416038 | 3/1997 |
| EP | 0629195 | 5/1999 |
| WO | 96/25667 | 8/1996 |

OTHER PUBLICATIONS

Adam, et al., J. Am. Chem. Soc., 118, 10400–10407 (1996).
Adam et al., J. Phys. Chem., 102, 5406–5414 (1998).
Adam, et al., J. Am., Chem. Soc., 121, 958–961 (1999).
Adam, et al., Biolumin. Chemilumin., Proc. Int. Symp., 10th, 33–36 (1999).
Bronstein, et al., J. Biolumin. Chemilumin., 44, 99–111 (1989).
Bronstein, et al., Properties of 1,2–dioxetane Chemiluminescence, 168–175 (2000).
Bronstein, et al., Clin. Chem., 42:9, 1542–1546 (1996).
Edwards, et al., J. Org. Chem., 55, 6225–6229 (1990).
Edwards, et al., J. Biolumin., Chemilumin., 5, 1–4 (1990).
Kobos, et al., Analytical Biochemistry, 224, 128–133 (1995).
Martin, et al., Biolumin. Chemilumin., Proc. Int. Symp., 9th, 525–528 (1997).
Olssen, et al., Methods in Enzymology, 305, 417–427 (2000).
Thorpe, et al., Clin. Chem., 35:12, 2319–2321 (1989).
Voyta, et al., Biolumin. Chemilumin. Proc. Int. Symp., 9th, 529–532 (1997).

* cited by examiner

Primary Examiner—Mary E. Ceperley
(74) Attorney, Agent, or Firm—Piper Rudnick LLP; Steven B. Kelber

(57) ABSTRACT

Chemiluminescent heteroaryl substituted benzothiazole 1,2-dioxetane compounds capable of producing light energy when decomposed are provided. These chemiluminescent compounds are represented by the general formula:

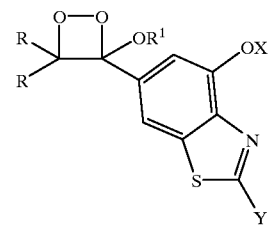

The heteroaryl substituent Y can be, for example, a pyridyl group or a benzothiazolyl group. The heteroaryl substituted benzothiazole compounds are substantially stable at room temperature. Kits including the heteroaryl substituted dioxetane compounds as well as methods for using these compounds for detecting the presence of one or more analytes in a sample are also provided.

29 Claims, 22 Drawing Sheets

BZPD

SYNTHESIS OF THE FUSED BENZOTHIAZOLE 1,2-DIOXETANE BZPD

PHOTOXYGENATION OF BENZOTHIAZOLE
ENOL ETHER PHOSPHATE

BENZYLOXY ENOL ETHER DERIVATIVES ALLOW REGIOSELECTIVE LIBERATION OF A PHENOL TO CREATE A LINKABLE GREEN-EMITTING SYSTEM

BENZOTHIAZOLE-DROX ENERGY TRANSFER ENZYME SUBSTRATE
O-ENZYME CLEAVABLE GROUP

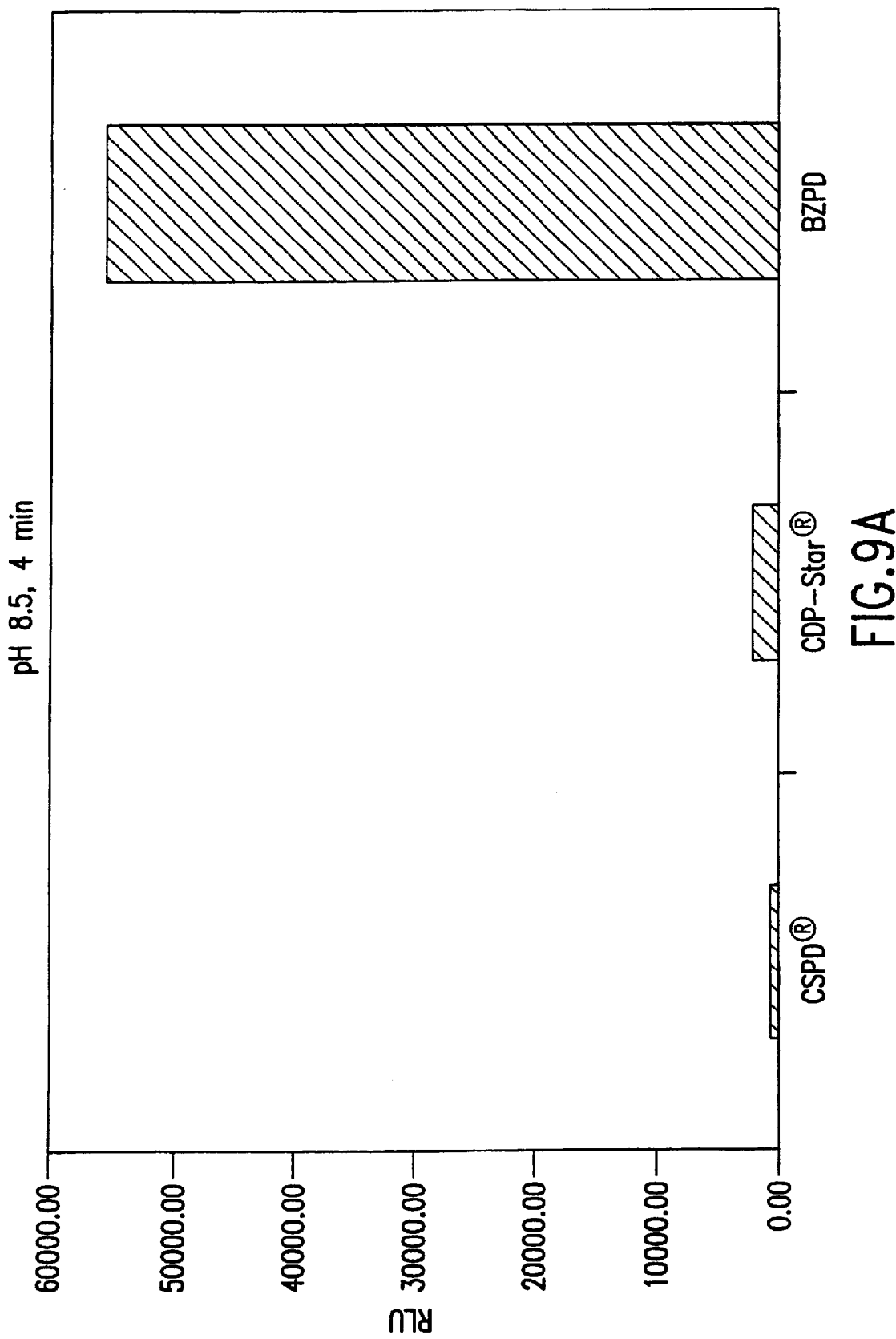

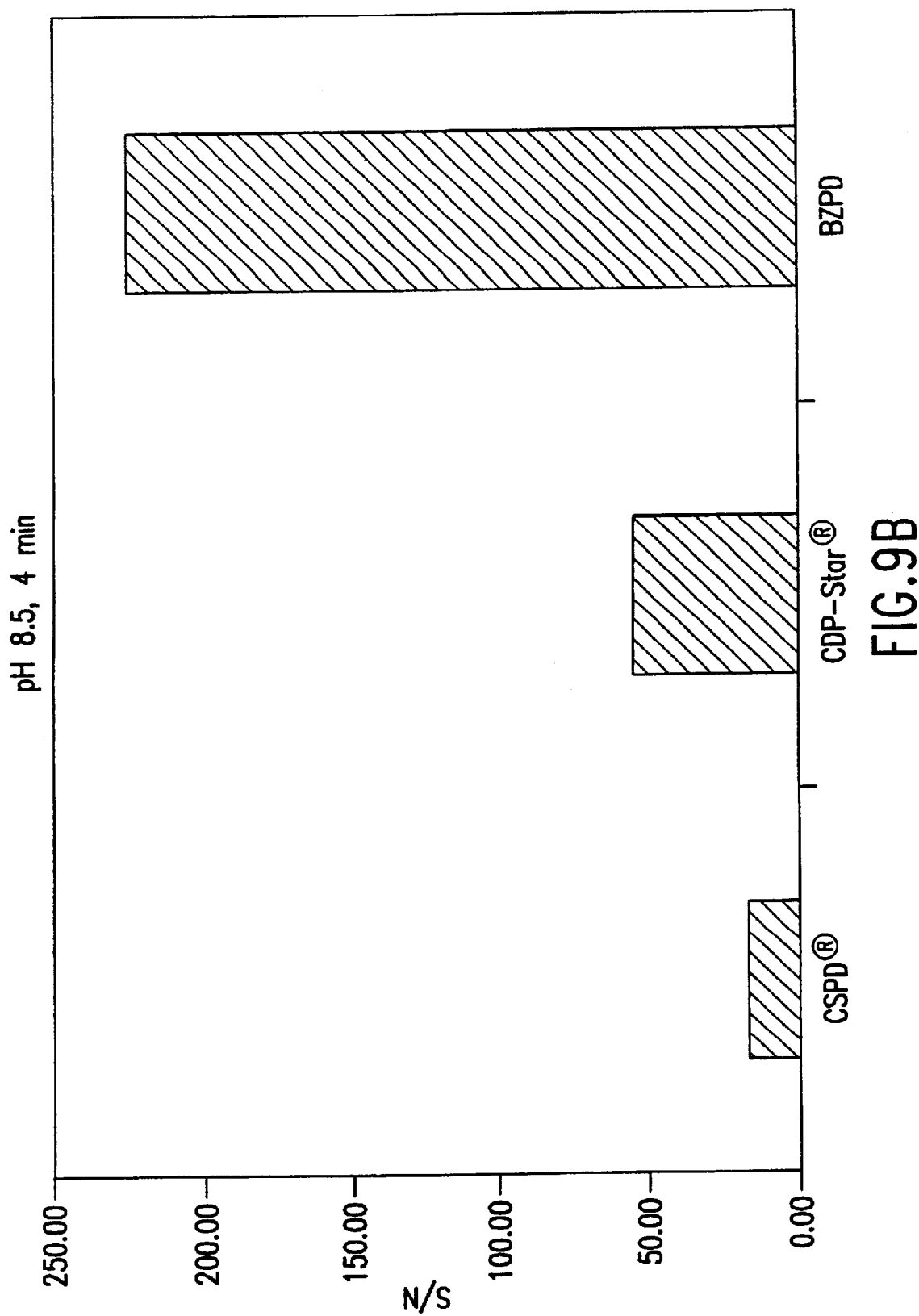

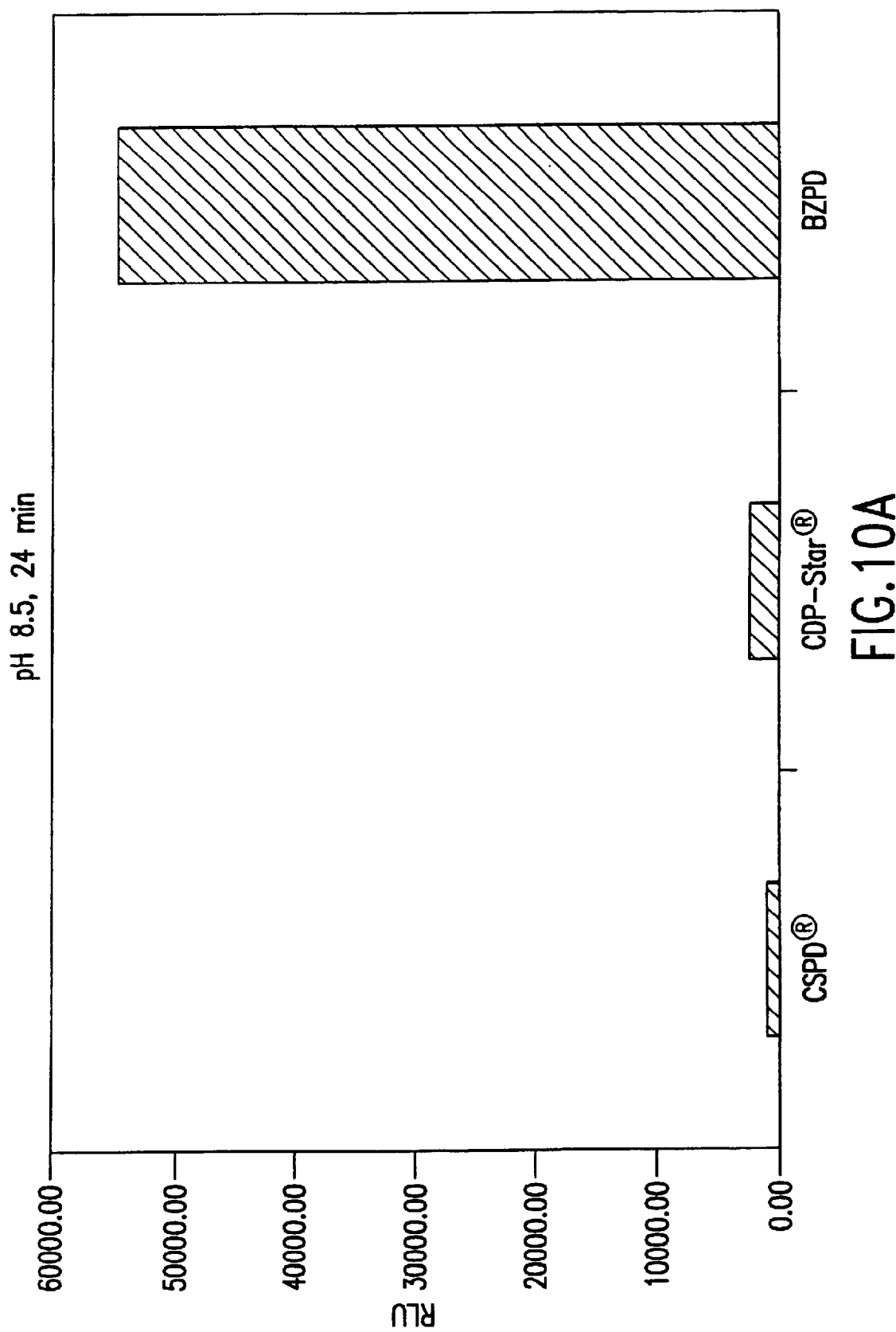

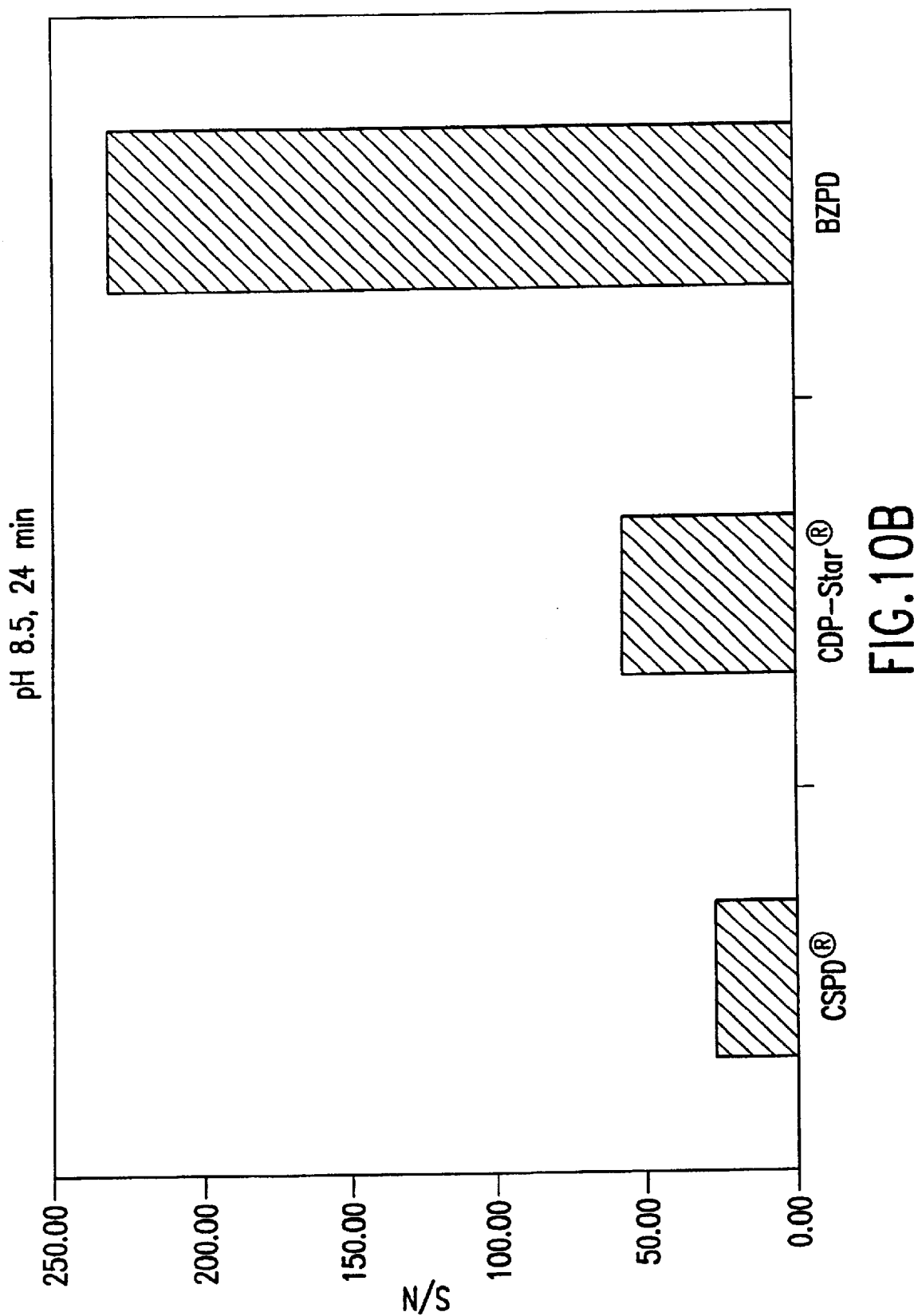

HETEROARYL SUBSTITUTED BENZOTHIAZOLE DIOXETANES

This application is a continuation-in-part of U.S. patent application Ser. No. 09/362,047, filed Jul. 28, 1999, now U.S. Pat. No. 6,355,441, which claims priority from Provisional Application No. 60/094,336, filed Jul. 28, 1998. The entirety of each application is incorporated herein by reference.

BACKGROUND OF THE INVENTION

1. Field of the Invention

This invention relates to improved chemiluminescent 1,2-dioxetane compounds. More particularly, this invention relates to improved enzymatically cleavable chemiluminescent 1,2-dioxetane compounds that contain enzymatically removable labile groups. Such labile groups prevent the molecule from decomposing to produce light, i.e., visible light or light detectable by appropriate instrumentation, until an appropriate enzyme is added to remove the labile group.

One enzyme molecule can affect the removal, through a catalytic cycle, of its complimentary labile group from thousands of enzymatically cleavable chemiluminescent 1,2-dioxetane molecules. This is a marked contrast to the situation with chemically cleavable chemiluminescent 1,2-dioxetanes, where one molecule of a chemical cleaving agent is needed to remove the complimentary labile group from each dioxetane molecule.

Enzymatically cleavable light-producing, 1,2-dioxetane compounds will usually also contain stabilizing groups, such as an adamantylidene group spiro bonded to the dioxetane ring's 3-carbon atom, that will aid in preventing the dioxetane compound from undergoing spontaneous decomposition at room temperature (about 25° C.) before the bond by which the enzymatically cleavable labile group is attached to the remainder of the molecule is intentionally cleaved. Wieringa. et al., *Tetahedron Letters*, 169 (1972), and McCapra, et al., *J. Chem. Soc., Chem.* Comm., 944 (1977). These stabilizing groups thus permit such dioxetanes to be stored for exceptionally long periods of time before use, e.g., for from about 12 months to as much as about 12 years at temperatures ranging from about 4° C. to about as much as 30 C., without undergoing substantial decomposition.

This invention further relates to the incorporation of its dioxetane molecules in art-recognized immunoassays, chemical assays and nucleic acid probe assays, and to their use as direct chemical/physical probes for studying the molecular structure or micro structures of various micromolecules, synthetic polymers, proteins, nucleic acids, catalytic antibodies, and the like, to permit an analyte (e.g., a chemical or biological substance whose presence, amount or structure is being determined) to be identified or quantified.

2. Background of the Invention

The use of 1,2-dioxetanes as chemiluminescent compounds is well established. These compounds, for example, have been used as reporters and labels in ultra sensitive assays for the detection of a variety of biological materials. By using 1,2-dioxetanes, these assays can be conducted quickly and without resort to exotic conditions or elaborate apparatus. See, for example, U.S. Pat. Nos. 4,931,223; 4,931,569; 4,952,707; 4,956,477; 4,978,614; 5,032,381; 5,145,772; 5,220,005; 5,225,584; 5,326,882; 5,330,900; 5,336,596; and 5,871,938. All of the foregoing are incorporated herein by reference. Other patents commonly assigned with this application have issued, and other applications are pending. Together, this wealth of patent literature addresses 1,2-dioxetanes stabilized by a typically polycyclic group, such as an adamantyl group spiro-bonded to one of the carbons of the dioxetane ring and another moiety (e.g., an aryl group) bonded to the remainder carbon of the dioxetane ring. This moiety is typically electron sensitive. Deprotection of the electron sensitive moiety results in the formation of an anion, generally an oxyanion, which is unstable and decomposes. Through decomposition, the O—O bond in the dioxetane is broken and a photon is generated. The same carbon atom to which this electron sensitive moiety is bonded may bear an alkoxy or other electron-active group.

The first of the dioxetanes of this class to be commercialized was 3-(4-methoxy-spiro(1,2-dioxetane-3,2'-tricyclo (3.3.1.1$^{3.7}$)decan)-4-yl)phenyl phosphate, particularly the disodium salt, generally known as AMPPD®. This compound has been commercialized by the assignee of this application, Tropix, Inc. of Bedford, Mass., as well as Lumigen, Inc. of Detroit, Mich. Superior performance of the above-described compounds can be obtained by selective substitution on the spiro-bound adamantane ring. For example, substitution at either bridgehead carbon with an electron active species, such as chlorine, has been found to improve reaction speed and signal to noise ratio (S/N). The chlorine substituted counterpart of AMPPD®, available under the trademark CSPD®, has also been widely commercialized by Tropix. "Third-generation" dioxetane compounds of similar structure, wherein the aryl moiety also bears an electron active substituent, such as chlorine, have been found to afford further improvements in performance. The 1,2-dioxetanes having aryl groups bearing phosphate moieties are available under the trademarks CSPD® and CDP-Star®, both of which are registered trademarks of Tropix, Inc.

Various materials have been used to enhance the chemiluminescent emissions of 1,2-dioxetanes. These materials, commonly referred to as chemiluminescent enhancing agents, include polymeric ammonium, phosphonium or sulphonium salts such as poly[vinyl benzyl(benzyldimethyl ammonium chloride)] ("BDMQ") and other hetero polar polymers.

It has been observed, however, that chemiluminescent dioxetanes such as AMPPD® in aqueous solution and also in the present chemiluminescent enhancers, may exhibit longer than optimum periods of time to reach constant light emission characteristics. The half-life or "$t_{1/2}$" of the active chemiluminescent species is defined as the time necessary to obtain one-half of the maximum chemiluminescence intensity at constant, steady-state light emission levels. This emission half-life can vary as a function of the stability of the dioxetane oxyanion in various environments. For example, the half-life of AMPPD® at concentrations above $2\times10^{-5}$ M in an aqueous solution at a pH 9.5 in the presence of BDMQ has been found to be approximately 7.5 minutes. At $4\times10^{-3}$ M in the absence of BDMQ, the $t_{1/2}$ of AMPPD® has been found to be approximately 30–60 minutes, while at $2\times10^{-5}$ M in an aqueous solution, the $t_{1/2}$ of AMPPD® has been found to be about 2.5 minutes.

Chemiluminescent intensity is typically measured after achieving steady state light emission kinetics. Statistically, approximately seven $t_{1/2}$ periods are required to reach steady-light emission kinetics. While chemiluminescent intensity can be measured before achieving steady state kinetics, sophisticated thermally-controlled luminometry instrumentation must be used if one wishes to acquire precise data prior to achieving steady-state emission kinetics. Therefore, in assays such as bioassays that employ enzymatically cleavable chemiluminescent 1,2-dioxetanes as reporter molecules, it is desirable to reach steady-state light emission kinetics as quickly as possible.

Furthermore, AMPPD®, in an aqueous buffered solution both in the presence and absence of chemiluminescent enhancers such as BDMQ, exhibits higher than desirable thermal and non-enzymatically activated light emission, or "noise." Such noise can be attributed to emission from the excited state adamantanone and of the methyl m-oxybenzoate anion derived from the aromatic portion of the AMPPD® molecule. The measured noise level of AMPPD® can be as much as two orders of magnitude above the dark current in a standard luminometer. This noise can therefore limit the levels of detection and prevent the realization of ultimate sensitivity in chemiluminescent assays.

Also, various instruments for detecting chemiluminescent emission such as charge coupled device (CCD) cameras have greater detection sensitivities in the green and red wavelengths. AMPPD® and related dioxetanes typically emit in the shorter wavelengths (e.g., blue wavelengths) of the visible spectrum. Heretofore, polymeric enhancers have been used to "shift" the emission wavelength toward the green or red end of the visible spectrum. It would therefore be desirable to obtain dioxetanes which emit radiation in wavelengths closer to the green portion or toward the red end of the visible spectrum to enhance detection sensitivity.

It is therefore an object of this invention to decrease the time necessary to conduct assays, and particularly bioassays, in which enzymatically cleavable chemiluminescent 1,2-dioxetanes are used as reporter molecules.

It is also an object of this invention to provide new and improved enzymatically cleavable chemiluminescent 1,2-dioxetanes which, when used as reporter molecules in assays, and in particular bioassays, reduce the time required to complete the assay.

A further object of this invention is to provide new and improved enzymatically cleavable chemiluminescent 1,2-dioxetanes for use as substrates for enzyme-based assays, and particularly bioassays, which provide improved signal to background behavior and thus provide improved detection levels.

A further object of this invention is the provision of dioxetane whose emission wavelengths are shifted toward the green and red wavelengths.

A still further object of this invention is to provide novel intermediates useful in synthesizing these improved enzymatically cleavable 1,2-dioxetanes.

Another object of this invention is to provide methods of preparing these enzymatically cleavable chemiluminescent 1,2-dioxetanes and intermediates thereof.

These and other objects, as well as the nature, scope and utilization of this invention, will become readily apparent to those skilled in the art from the following description and the appended claims.

SUMMARY OF THE INVENTION

According to a first aspect of the invention, a chemiluminescent compound of the general formula set forth below is provided.

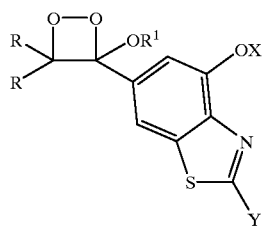

Each of the substituents R in the above formula may independently be a branched alkyl or cycloalkyl group which provides stabilization for the dioxetane. Alternatively, both R groups may be joined in a cycloalkyl or polycycloalkyl moiety spiro bound to the dioxetane ring. Each of the R groups or the spiro bound cyclic group may be unsubstituted or substituted with a halogen atom, an alkoxy group, or an electron-withdrawing organic group. The substituent $R^1$ can be an aryl group or an alkyl group of 1–20 carbon atoms, which may be optionally substituted with one or more halogen atoms. The substituent X may be any protecting group which is removable by chemical or enzymatic means. According to a preferred embodiment of the invention, Y is a heterocyclic aromatic moiety (i.e., a heteroaryl group). According to a further preferred embodiment of the invention, the heterocyclic aromatic moiety Y is: 2-, 3-, or 4-pyridyl; 2-benzothiazolyl; 2-benzoxazolyl; 2-benzofuranyl; 2-benzothienyl; 2-, 4-, or 5-thiazolyl; 3-, 4-, 5-, 6-, or 7-quinolinyl; 3-, 4-, or 5-isoxazolyl; 3-, 4-, or 5-isothiazolyl; or 2-, 4-, 5-, or 6-pyrimidinyl.

According to a second aspect of the invention, a kit for detecting the presence of an analyte in a sample is provided. The kit includes the 1,2-dioxetane compound set forth above. The kit according to the invention can further include a substance such as an enzyme which, in the presence of the dioxetane compound, causes the dioxetane compound to decompose and generate light.

According to a third aspect of the invention, a method for detecting the presence of an analyte in a sample is provided. The method includes adding the dioxetane compound set forth above to the sample wherein the moiety X can be removed by the analyte. The method further includes incubating the sample and inspecting the sample for generated light. The presence of generated light indicates the presence of the substance. The amount of light detected can be used to determine the amount of the substance present in the sample. Methods for simultaneously detecting the presence of two or more analytes in a sample are also provided.

BRIEF DESCRIPTION OF THE DRAWINGS

FIG. 9A shows luminescence (RLU) values for CSPD®, CDP-Star® and BZPD at a pH of 8.5 and at a time of 4 min.;

FIG. 9B shows the signal to noise ratio (S/N) for the luminescence of CSPD®, CDP-Star® and BZPD at a pH of 8.5 and at a time of 4 min.;

FIG. 10A shows luminescence (RLU) values for CSPD®, CDP-Star® and BZPD at a pH of 8.5 and at a time of 24 min.;

FIG. 10B shows the signal to noise ratio (S/N) for the luminescence of CSPD®, CDP-Star® and BZPD at a pH of 8.5 and at a time of 24 min.;

DETAILED DESCRIPTION

Figure 1:
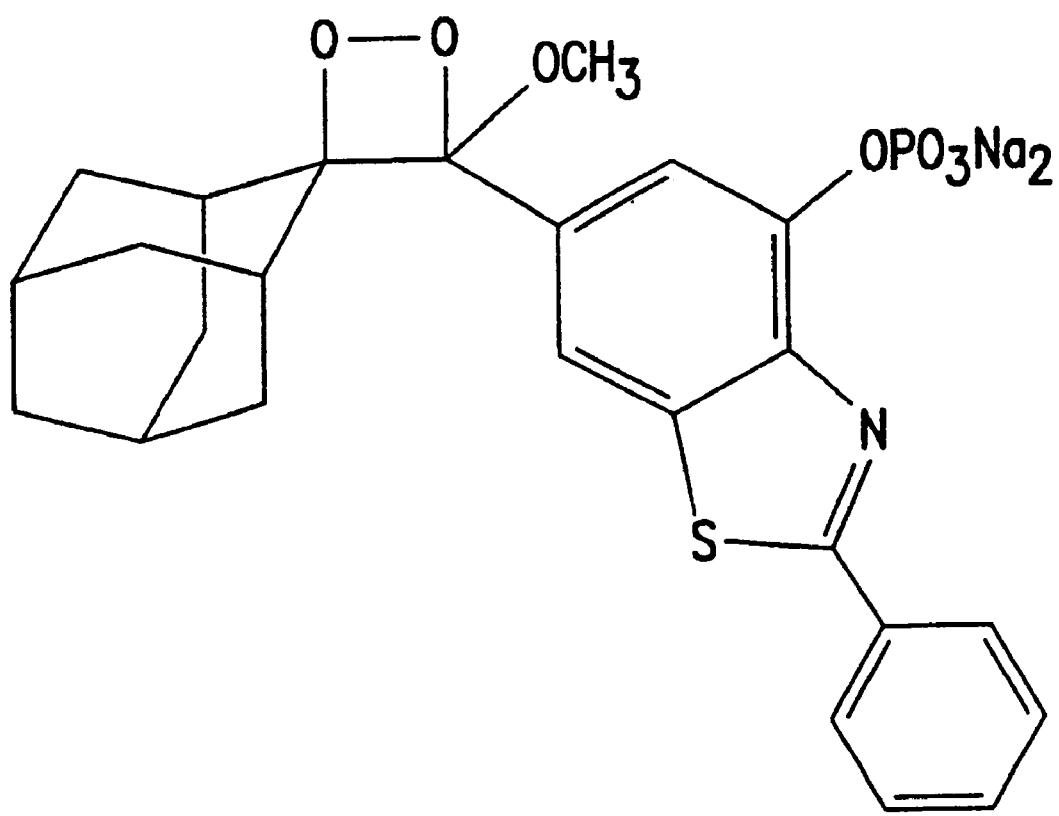
FIG. 1 shows the chemical structure of a benzothiazole 1,2-dioxetane phosphate (BZPD)

We now describe the structure, synthesis, and use of preferred embodiments of the present invention.

According to the invention, a chemiluminescent compound having the general formula (I) is provided:

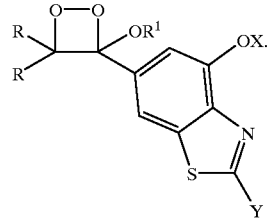

(I)

In general formula (I) above, each R may independently be any branched alkyl or cycloalkyl group which provides stabilization for the dioxetane. Alternatively, both R groups together can form a cycloalkyl or polycycloalkyl moiety Spiro bound to the dioxetane ring. Each of the R groups may be substituted or unsubstituted. Further, if the R groups form a spiro bound cyclic moiety, the spiro bound cyclic moiety may be substituted or unsubstituted. The R groups or the spiro bound cyclic group may be substituted, for example, with a halogen atom, an alkoxy group, or an electron-withdrawing organic group. The substituent $R^1$ can be an aryl group or an alkyl group having 1–20 carbon atoms, which may be optionally substituted with one or more halogen atoms. According to the invention, the substituent Y on the 2-carbon of the benzothiazole moiety is a heteroaryl group. The heteroaryl group can be substituted with electron active groups or solubilizing groups. The substituent X may be any protecting group which is removed by chemical or enzymatic means.

According to a second aspect of the invention, a chemiluminescent compound having the general formula (II) is provided:

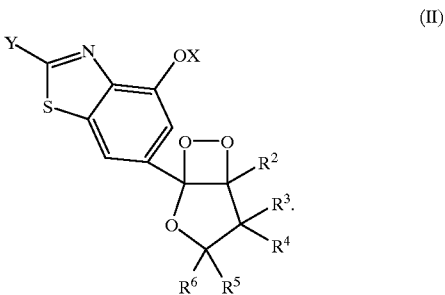

(II)

The substituents X and Y in Formula II are defined as set forth above for Formula I. The substituents $R^2$–$R^6$ in Formula (II) above can independently be hydrogen, alkyl, substituted alkyl, aryl, or substituted aryl. Further, the substituents $R^3$ and $R^4$ may be joined as a spiro-fused cycloalkyl group.

The dioxetanes according to Formula II of the invention can be synthesized by way of the corresponding benzothiazole aldehyde or toluene derivative using permanganate oxidation to provide a carboxylic acid. Esters of this carboxylic acid can then be used to prepare dioxetane precursors for t he above compounds. Methods of this type are described in U.S. Pat. No. 5,731,445, which is incorporated herein by reference.

Representative identities for each of the substituents of formulas I and II will be familiar to those of skill in the art, given the novel chemical formulas herein and the earlier patents of Tropix incorporated herein by reference. Preferred identities for R include straight or branched chain alkyls of 2–12 carbon atoms. Branched alkyl groups are preferred.

Further, each alkyl group may be substituted with one or more electron-withdrawing or electron-donating groups, and/or each alkyl moiety R may be substituted with one or more groups which increase the solubility of the overall dioxetane, which is generally quite hydrophobic. Preferred solubilizing groups include carboxylic acid moieties, sulfonic acid moieties, phosphoric acid moieties, ammonium moieties, etc.

In a preferred embodiment, both R groups together form a spiro bound adamantyl group, which may be unsubstituted or substituted at either or both bridgehead carbons with an electron-active (i.e., an electron-withdrawing or an electron-donating) group. Suitable electron active groups include alkoxy groups having 1–7 carbon atoms, halo groups, alkyl groups, etc. Exemplary substituents on the adamantyl group are set forth in U.S. Pat. No. 5,112,960, which is incorporated herein by reference. Further, the identity of each group R can be selected so as to provide steric stabilization for the dioxetane to prevent premature decomposition.

The substituents $R^2$–$R^6$ can each be independently selected with the exception that $R^3$ and $R^4$ may be joined to form a spiro-fused cycloalkyl group, as described above for the R groups of Formula I. Otherwise, $R^2$–$R^6$ can be independently selected from hydrogen, alkyl groups of 1–6 carbon atoms which are unsubstituted or substituted with one or more halogen groups (e.g., trifluroalkyl), hydroxy, phenyl, naphthyl, etc. Any of the moieties $R^2$–$R^6$, either alone or in combination, may be further substituted with one or more groups calculated to enhance the water solubility of the dioxetane, as described above. Further, each moiety $R^2$–$R^6$ may bear one or two water solubility-enhancing groups. Instead of alkyl, each and/or all of $R^2$–$R^6$ may be an aryl group, preferably phenyl.

The heteroaryl group Y can be substituted with electron active groups. Preferred electron-active substituents on Y include chloro, aralkenyl, alkoxy (—OR), aryloxy (—OAr), trialkylammonium (—NR$_3$+), alkylamido (—NHCOR, —NRCOR'), arylamido (—NHCOAr, —NRCOAr, —NarCOAr), arylcarbamoyl (—NHCOOAr, —NRCOOAr), alkylcarbamoyl (—NHCOOR, —NRCOOR'), cyano (—CN), nitro (—NO$_2$), ester (—COOR, —COOAr), alkyl- or arylsulfonamido (—NHSO$_2$R, —NHSO$_2$Ar), trifluoromethyl (—CF$_3$), aryl (—Ar), alkyl (—R), trialkyl-, triaryl-, or alkylarysilyl (—SiR$_3$, —SiAr$_3$, —SiArR$_2$), alkyl- or arylamidosulfonyl (—SO$_2$NHCOR, —SO$_2$NHCOAr), alkyl- or arylsulfonyl (—SO$_2$Ar), alkyl- or arylthioethers (—SR, —SAr). The size of the Z substituent is generally limited only by solubility concerns. Where reference is made to alkyl or R, R', etc., the alkyl moiety preferably has from 1–12 carbon atoms. Suitable aryl moieties include phenyl and naphthyl. Particularly preferred electron active substituents include chloro and alkoxy.

The heteroaryl group Y can also be substituted with water solubilizing groups such as carboxylic acids, sulfates, sulfonates, phosphates, and ammonium groups. The water solubility of Y can also be increased by alkylation of one of the heteroatoms in Y to produce a quaternized heteroaryl group.

As set forth in the aforementioned U.S. Pat. No. 5,538,847, electron-donating groups, such as methoxy groups, enhance the anion decomposition process, whereas electron-withdrawing groups, such as chlorine, may retard the same decomposition reaction. Surprisingly, the influence of substituents on the aryl ring may have the opposite effect to substituents on the adamantyl group or other steric stabilizing group.

According to the invention, Y is an aromatic heterocyclic (e.g., heteroaryl) group. Particularly suitable heteroaryl groups include 2-, 3-, or 4-pyridyl; 2-benzothiazolyl; 2-benzoxazolyl; 2-benzofuranyl; 2-benzothienyl; 2-, 4-, or 5-thiazolyl; 3-, 4-, or 5-isoxazolyl; 3-, 4-, or 5-isothiazolyl; 3-, 4-, 5-, 6- or 7-quinolinyl; or 2-, 4-, 5-, or 6-pyrimidinyl. The heteroaryl group Y according to the invention can be either unsubstituted or substituted. Preferred substituents for the heteroaryl group include one or more electron active groups.

Typically, the X substituent in Formulae I and II above is an enzyme-labile group. Although preferred enzyme-labile groups include phosphate moieties and galactoside moieties, virtually any enzyme-cleavable group, which, upon cleavage, leaves an oxyanion, is suitable for use in the invention. A large variety of enzyme-cleavable groups are set forth in U.S. Pat. No. 5,605,795, which is incorporated herein by reference. In general, in addition to the phosphate esters, moiety X may be any of the moieties identified for group Z in U.S. Pat. No. 5,605,795, incorporated herein by reference, including substrates for esterases, decarboxylases, phospholipases, α- or β-xylosidase, fucosidases, glucosidases, and thioglucosidases, galactosidases, mannosidases, fructofuranosidases, glucosiduronases, trypsin, etc. Additionally, the moiety-OX can be replaced by any of a wide variety of peptides cleavable by proteolytic enzymes, such as those set forth in U.S. Pat. No. 5,591,591, which is incorporated herein by reference.

As previously noted, there are situations where non-enzymatic chemical triggering, as opposed to enzymatic triggering, may be desired. In these instances, the X substituent can be, for example, H, trialkylsilyl, etc. Chemical triggering, as well as various identities for the substituent X, are disclosed in U.S. Pat. No. 5,652,345, which is also incorporated herein by reference.

In monitoring, and measuring (e.g., quantifying) chemiluminescence, a wide variety of apparatuses have been developed. Among the most sensitive, and particularly suited to high throughput screening applications and the like, are CCD cameras. Typical luminescent emission from dioxetanes is in the blue wavelengths of the visible spectrum. CCD cameras, however, can have difficulty registering blue emissions. Therefore, only the "edge" of the longer wavelengths of the blue emission are typically observed by the camera. By employing a benzothiazole resonating moiety on the dioxetane according to the invention, the light being emitted can be green-shifted. That is, the emission can be shifted toward the green or red region of the visible spectrum.

Prior art dioxetanes are typically used with enhancement agents which act to sequester the dioxetane in hydrophobic regions thus reducing the chemiluminescent quenching that can be observed in the presence of water. These enhancement molecules are preferably onium quaternary polymers such as phosphonium, sulfonium and ammonium polymers. Representative polymers, and their effects, are set forth in U.S. Pat. No. 5,330,900, which is incorporated herein by reference. These polymers may be used alone, or together with a surfactant additive, to further improve the enhancement value, as disclosed in U.S. Pat. No. 5,547,836, which is also incorporated herein by reference.

In the present invention, as a result of the green shifting of the dioxetane emission, and the enhanced hydrophobicity of the dioxetanes due to the presence of the fused benzothiazole ring, lower concentrations of enhancement agents and other additives can be used.

Referring more particularly to the figures, FIG. 1 shows the general formula for the chemical structure of benzothiazole dioxetane phosphate. This molecule is referred to herein as BZPD. The BZPD molecule shown in FIG. 1 has a phenyl substituent at the 2 position of the benzothiazole group. According to the invention, however, other substituents can be used on the benzothiazole. Preferred substituents according to the invention are aromatic heterocyclic (e.g. heteroaryl) groups such as pyridyl, benzothiazolyl, benzoxazolyl, etc. According to a preferred embodiment of the invention, the heterocyclic aromatic moiety is 2-, 3-, or 4-pyridyl; 2-benzothiazolyl; 2-benzoxazolyl; 2-benzofuranyl; 2-benzothienyl; 2-, 4-, or 5-thiazolyl; 3-, 4-, or 5-isoxazolyl; 3-, 4-, or 5-isothiazolyl; 3-, 4-, 5-, 6-, or 7-quinolinyl; or 2-, 4-, 5-, or 6-pyrimidinyl.

The synthesis methods illustrated in FIGS. 2–6 and described below are directed to a BZPD dioxetane with a phenyl or substituted phenyl substituent. However, these techniques could be adapted to synthesize a similar dioxetane molecule having a heteroaryl substituent on the benzothiazole group according to the invention. Adaptation of the techniques illustrated in FIGS. 2–6 would be within the level of ordinary skill in the art.

Figure 2A:
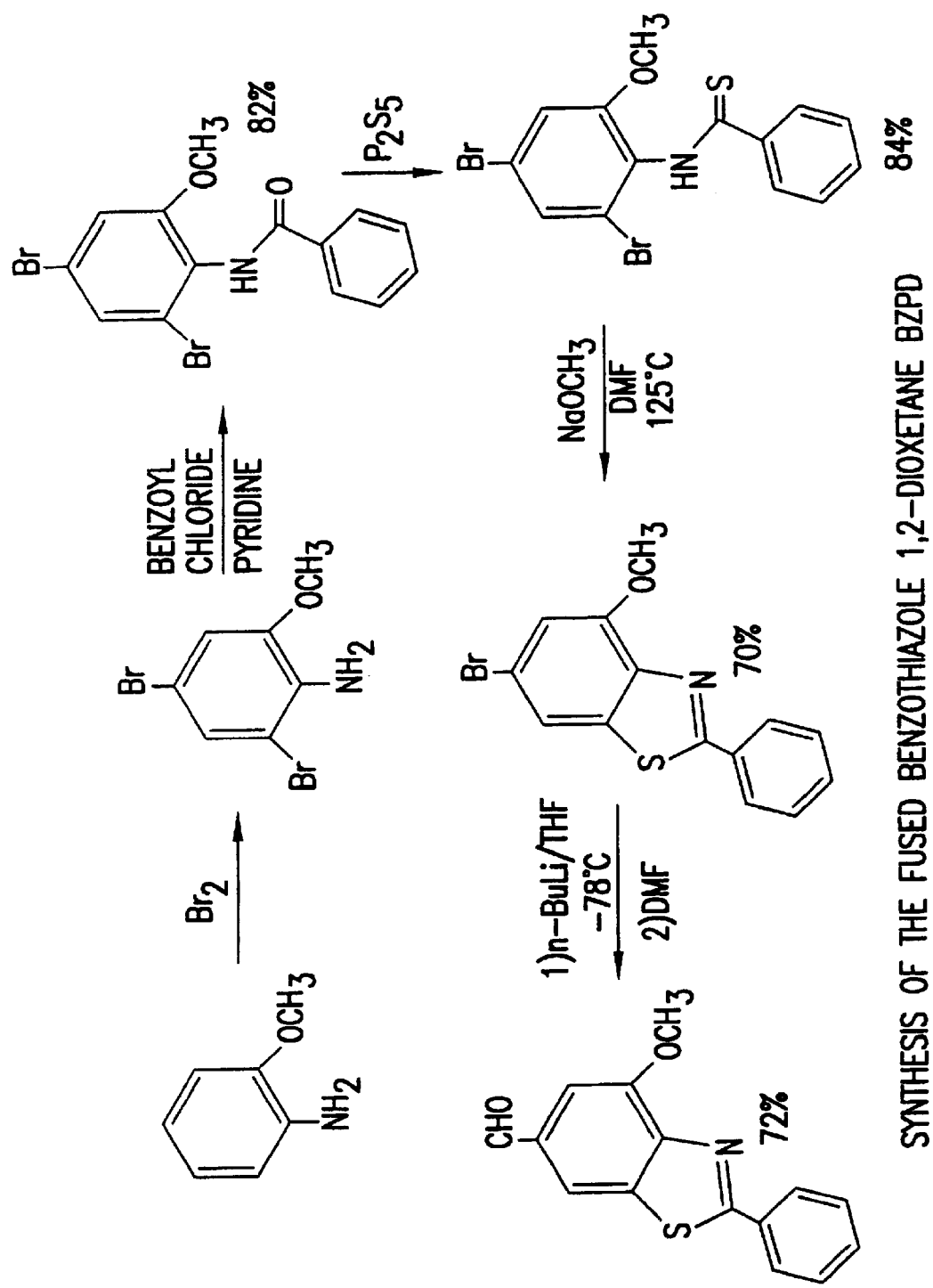
FIG. 2A shows a first set of steps for the synthesis of the fused benzothiazole 1,2-dioxetane phosphate (BZPD) of FIG. 1 including the synthesis of a benzothiazole compound with a phenyl substituent.
Figure 2B:
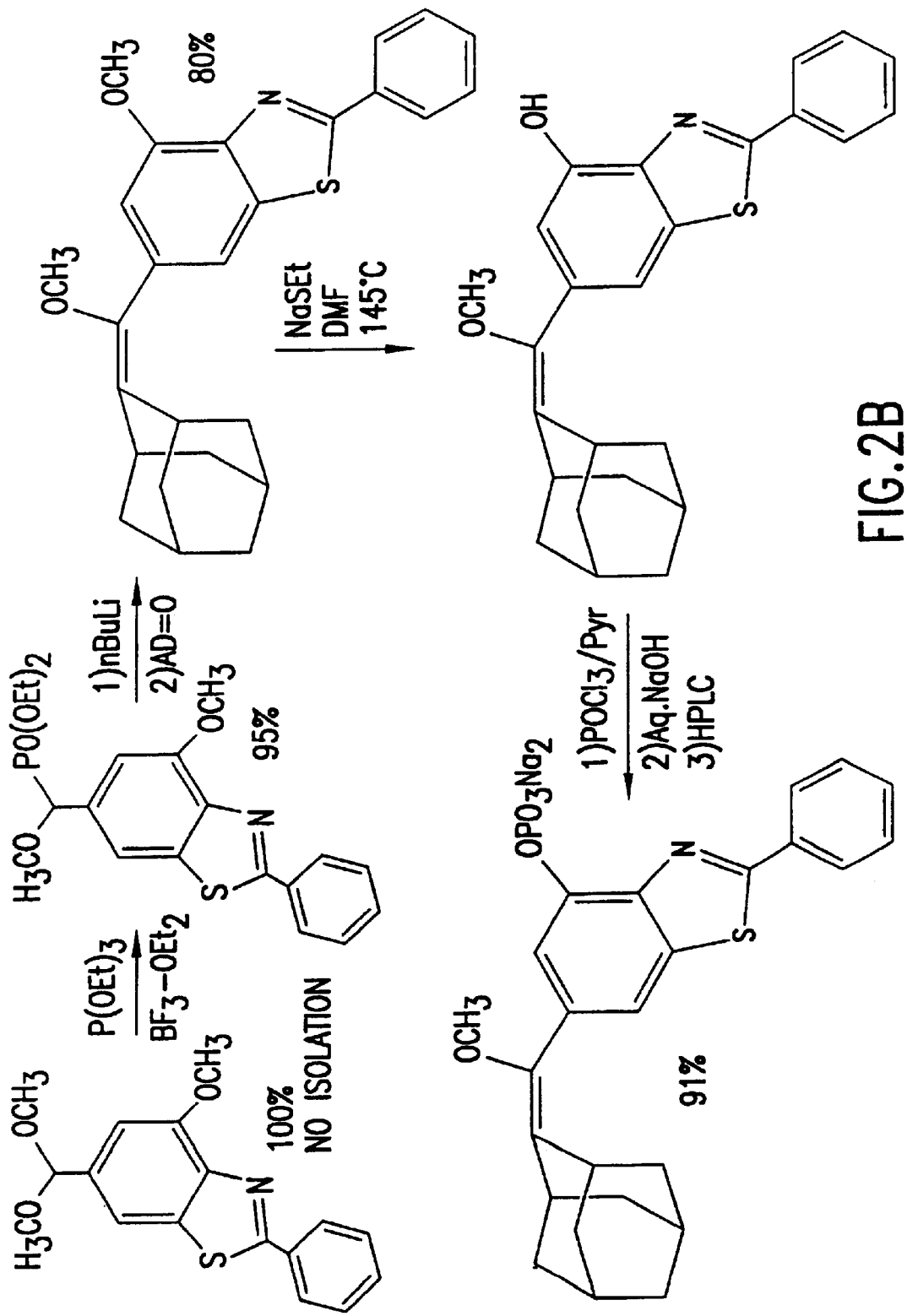
FIG. 2B shows a second set of steps for the synthesis of the fused benzothiazole 1,2-dioxetane phosphate (BZPD) of FIG. 1 including the synthesis of the corresponding benzothiazole enol ether phosphate.
Figure 3:
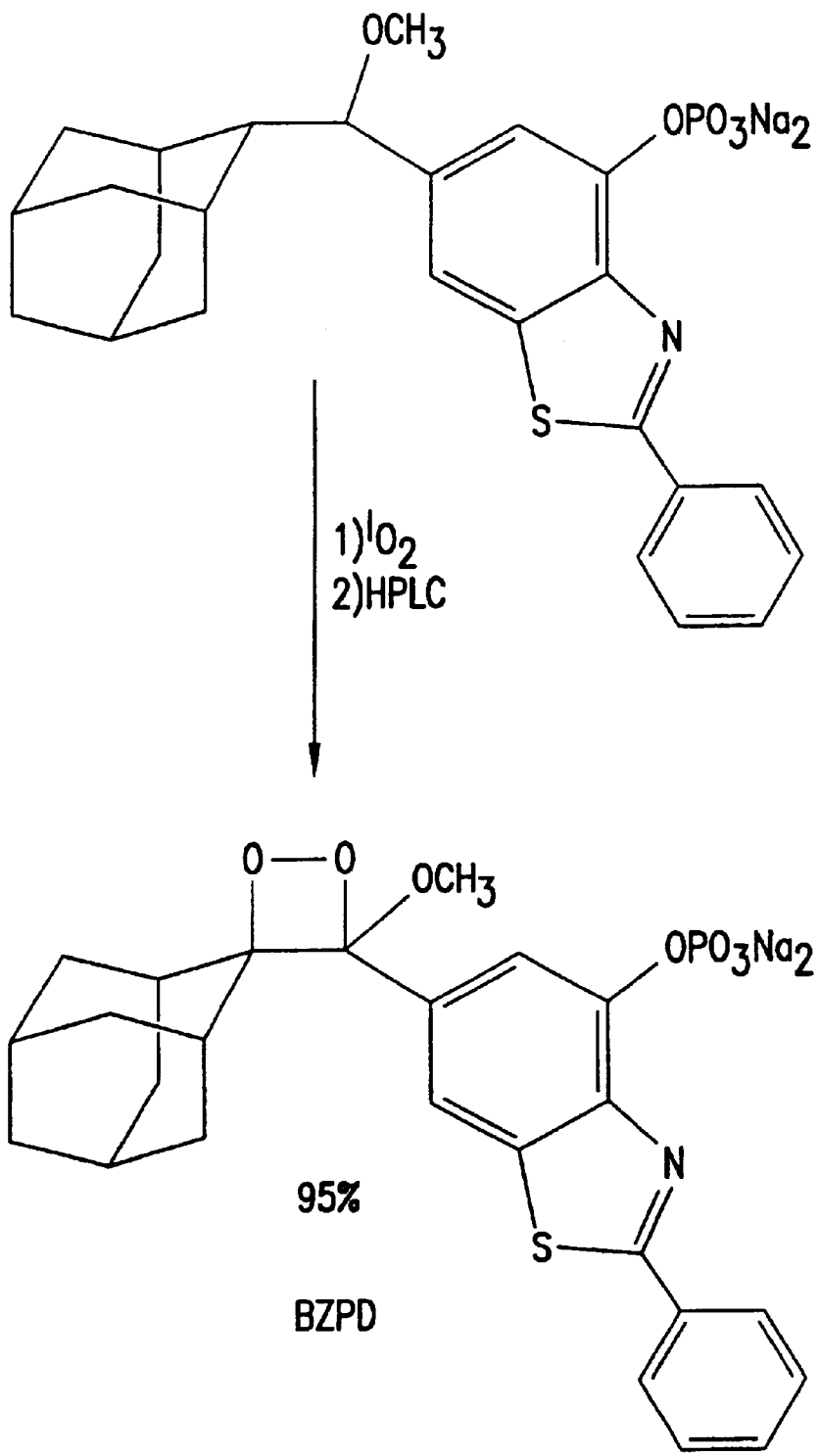
FIG. 3 shows a final step for the synthesis of the fused benzothiazole 1,2-dioxetane phosphate (BZPD) of FIG. 1 including a step of photoxygenation of the corresponding benzothiazole enol ether phosphate.

The synthesis of the BZPD dioxetane of FIG. 1 is illustrated in FIGS. 2A, 2B and 3. FIG. 2A shows a first set of steps for the synthesis of the fused benzothiazole 1,2-dioxetane phosphate (BZPD) of FIG. 1 including the synthesis of a benzothiazole compound with a phenyl substituent. FIG. 2B shows a second set of steps for the synthesis of the fused benzothiazole 1,2-dioxetane phosphate (BZPD) of FIG. 1 including the synthesis of the corresponding benzothiazole enol ether phosphate. FIG. 3 shows a final step for the synthesis of the fused benzothiazole 1,2-dioxetane phosphate (BZPD) of FIG. 1 including a step of photooxygenation of the corresponding benzothiazole enol ether phosphate.

Figure 4:
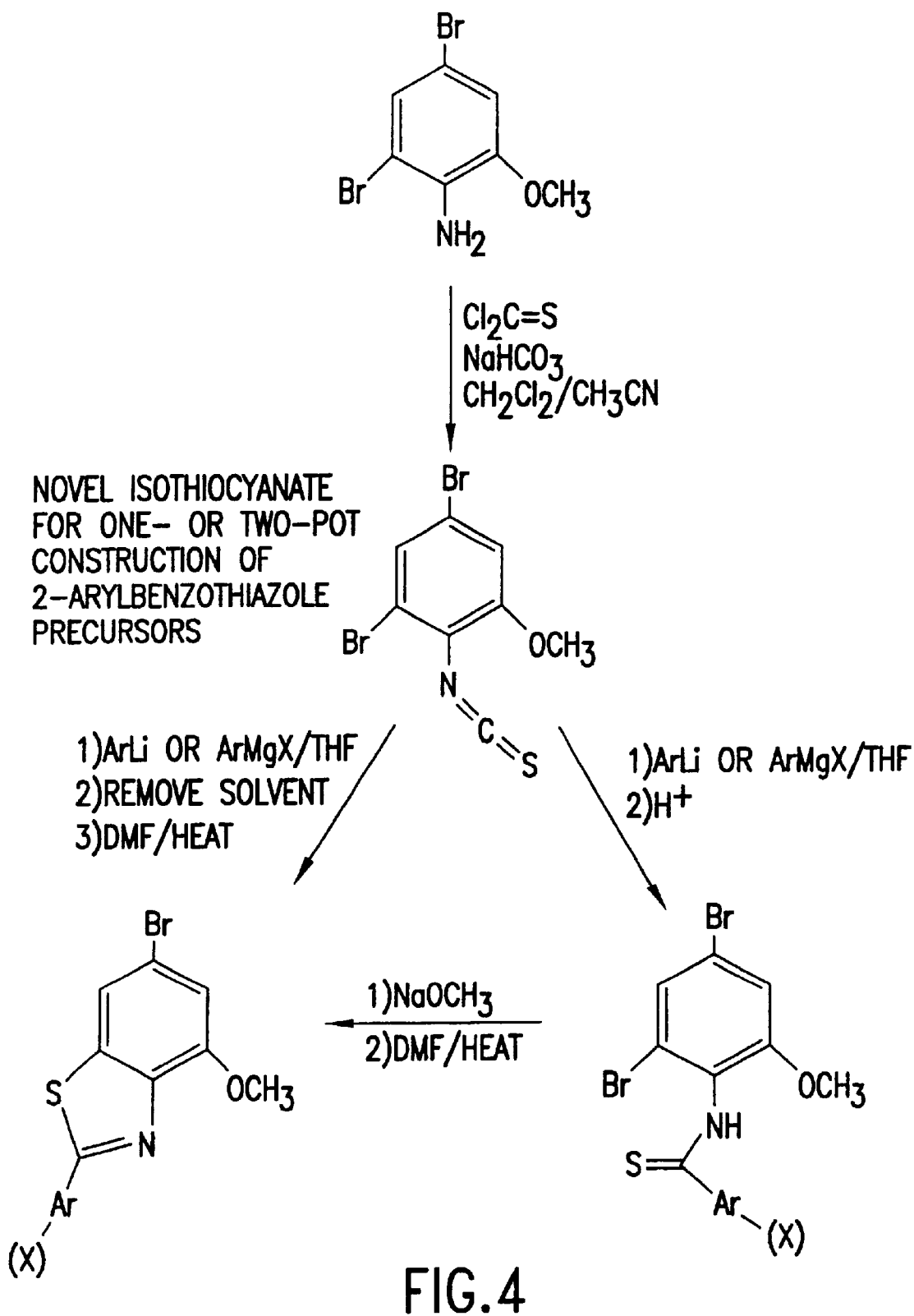
FIG. 4 illustrates the synthesis of a benzothiazole compound with an aryl substituent.

Although conventional starting materials may be used to synthesize the dioxetanes of the present invention, novel isothiocyanates are set forth as an aspect of the invention and are illustrated in FIG. 4 wherein the synthesis of a benzothiazole compound with an aryl substituent is illustrated.

Figure 5:
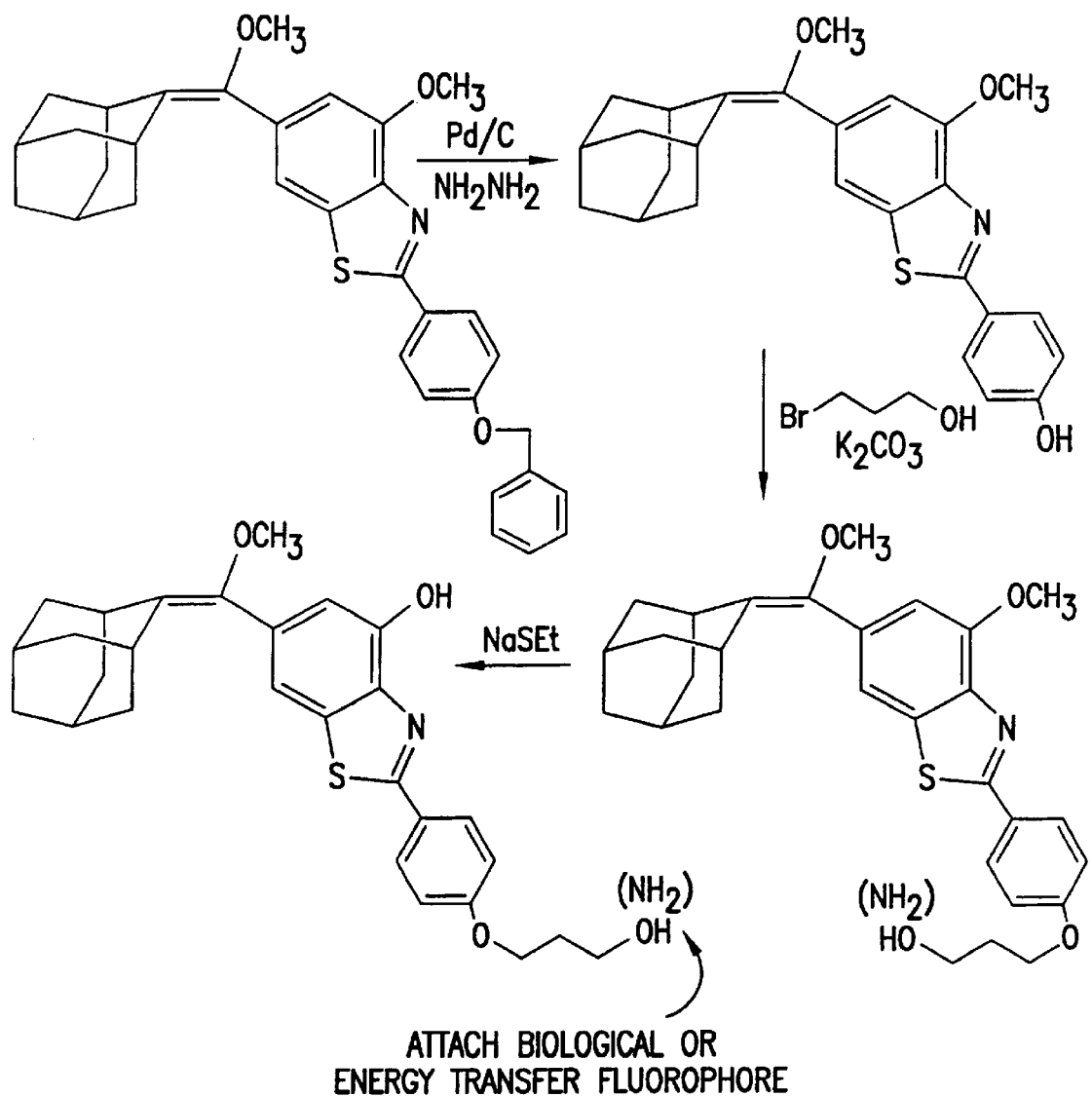
FIG. 5 illustrates the synthesis of a benzothiazole enol ether derivative with a benzyloxy linker for attachment of a biological moiety or an energy transfer fluorophore.

FIG. 5 illustrates the synthesis of a benzyloxy benzothiazole enol ether derivative which can be used to synthesize a dioxetane having a site for attachment of a biological moiety or an energy transfer fluorophore according to the invention.

Figure 6:
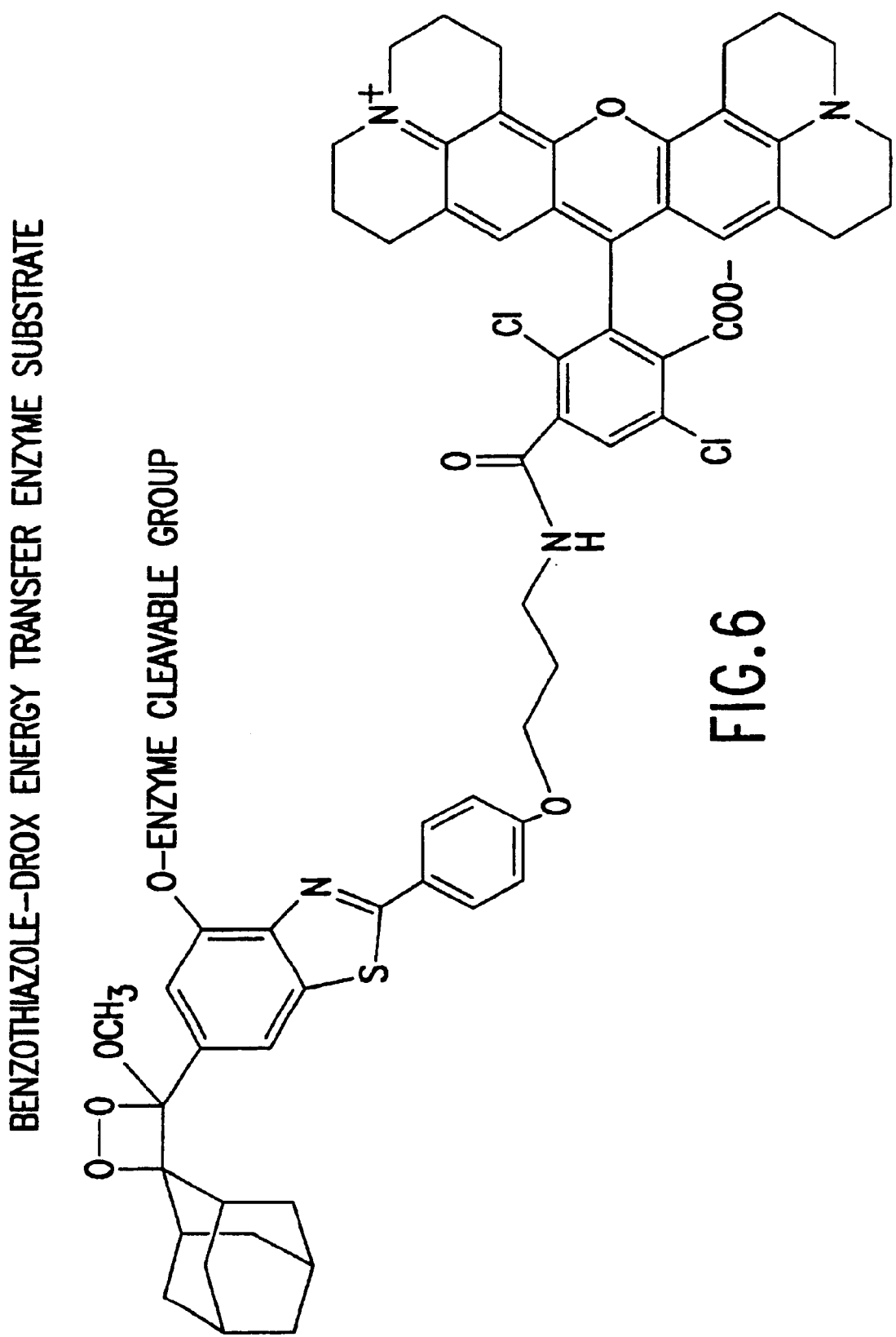
FIG. 6 shows a benzothiazole-DROX energy transfer enzyme substrate.

FIG. 6 shows a benzothiazole-DROX energy transfer enzyme substrate.

Figure 7:
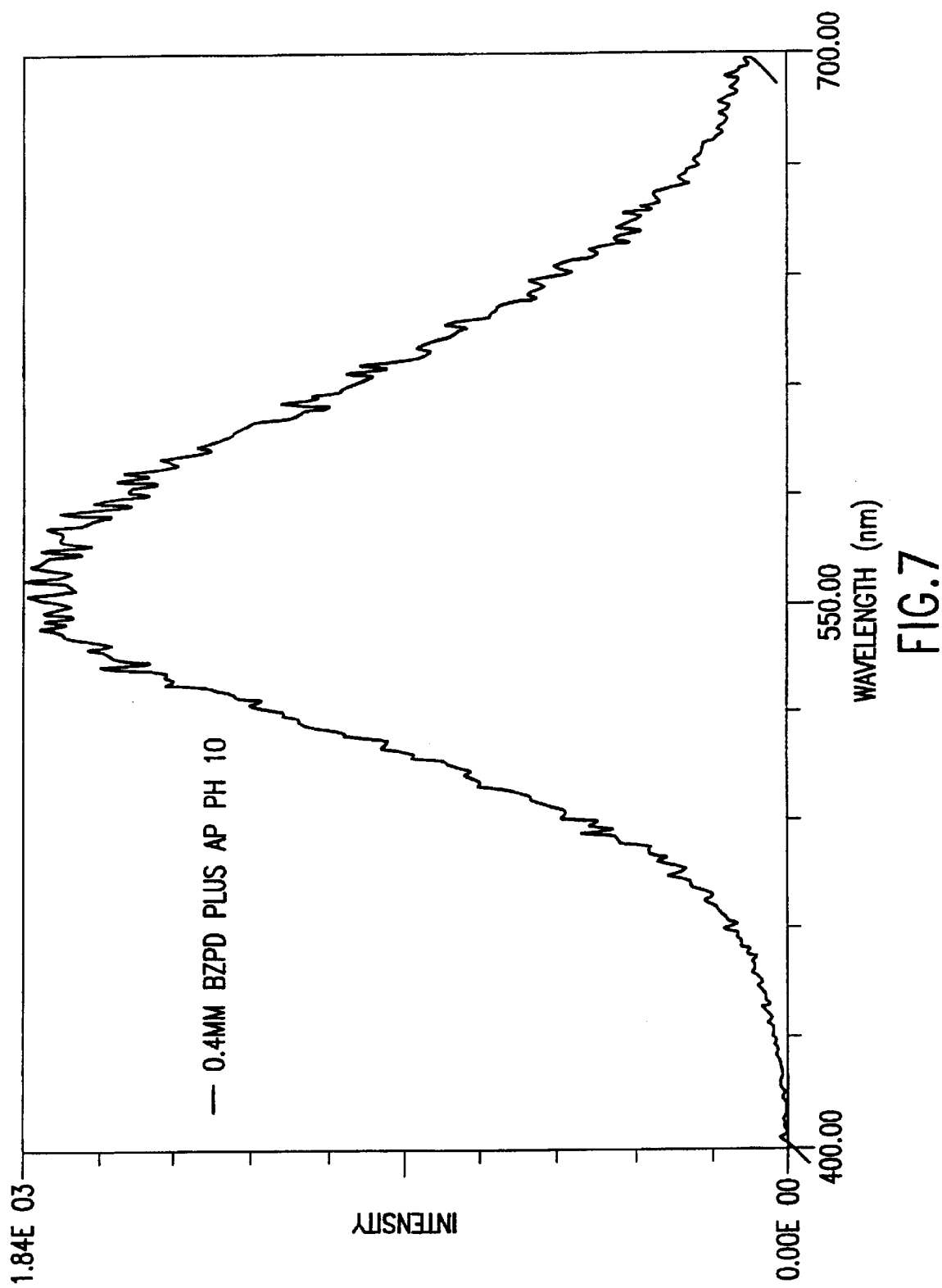
FIG. 7 shows the emission spectrum of the dioxetane of FIG. 1 in the presence of alkaline phosphatase at a pH of 10.
Figure 8:
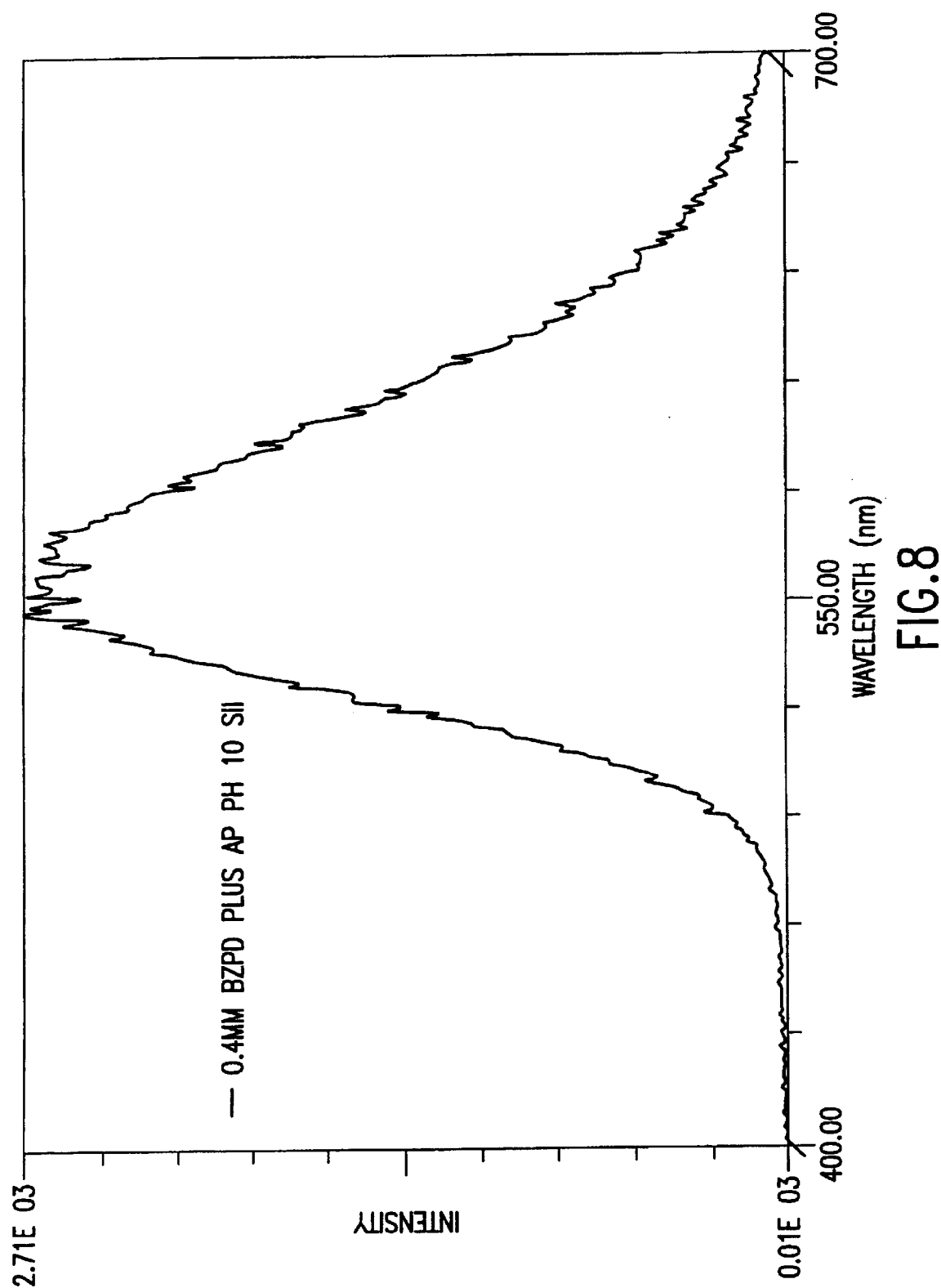
FIG. 8 shows the emission spectrum of the dioxetane of FIG. 1 in the presence of alkaline phosphatase at a pH of 10.

FIGS. 7 and 8 show the intensity of emissions as a function of wavelength for BZPD. FIG. 7 illustrates the "green shifting" of the wavelength emission of BZPD, showing a peak wavelength above 550 nm, in the absence of any enhancement agent. FIG. 8 illustrates that, in the presence of an enhancement agent (i.e., Sapphire-II™), long wavelength intensity of the chemiluminescent emissions can be further enhanced.

The relative chemiluminescent performance of BZPD is compared with other commercially available dioxetanes in FIGS. 9–12. FIG. 9A shows luminscence (RLU) at a pH of 8.5 and at a time of 4 minutes for BZPD compared to CSPD® (a phenyl dioxetane bearing a chlorine substituent on the adamantyl group) and CDP-Star® (a phenyl dioxetane bearing chlorine substituents on both the adamantyl group and on the phenyl moiety). As can be seen from FIG. 9A, the half-life ($t_{1/2}$) of BZPD is shorter than the corresponding half-life of CSPD® or CDP-Star®. As shown in FIG. 9B, the inventive dioxetanes also have an excellent signal to noise ratio (S/N) under these conditions. The signal to noise ratio (S/N) values are important because if the background noise is too high (i.e., if the S/N is too low) the assay can be relatively insensitive no matter how rapidly the peak intensity is developed.

FIGS. 10A and 10B show the luminescence value and S/N after at a pH of 8.5 and at a time of 24 minutes. As can be seen from these figures, BZPD exhibits a significantly higher luminescence and a significantly higher sensitivity (S/N) under these conditions.

Figure 11A:
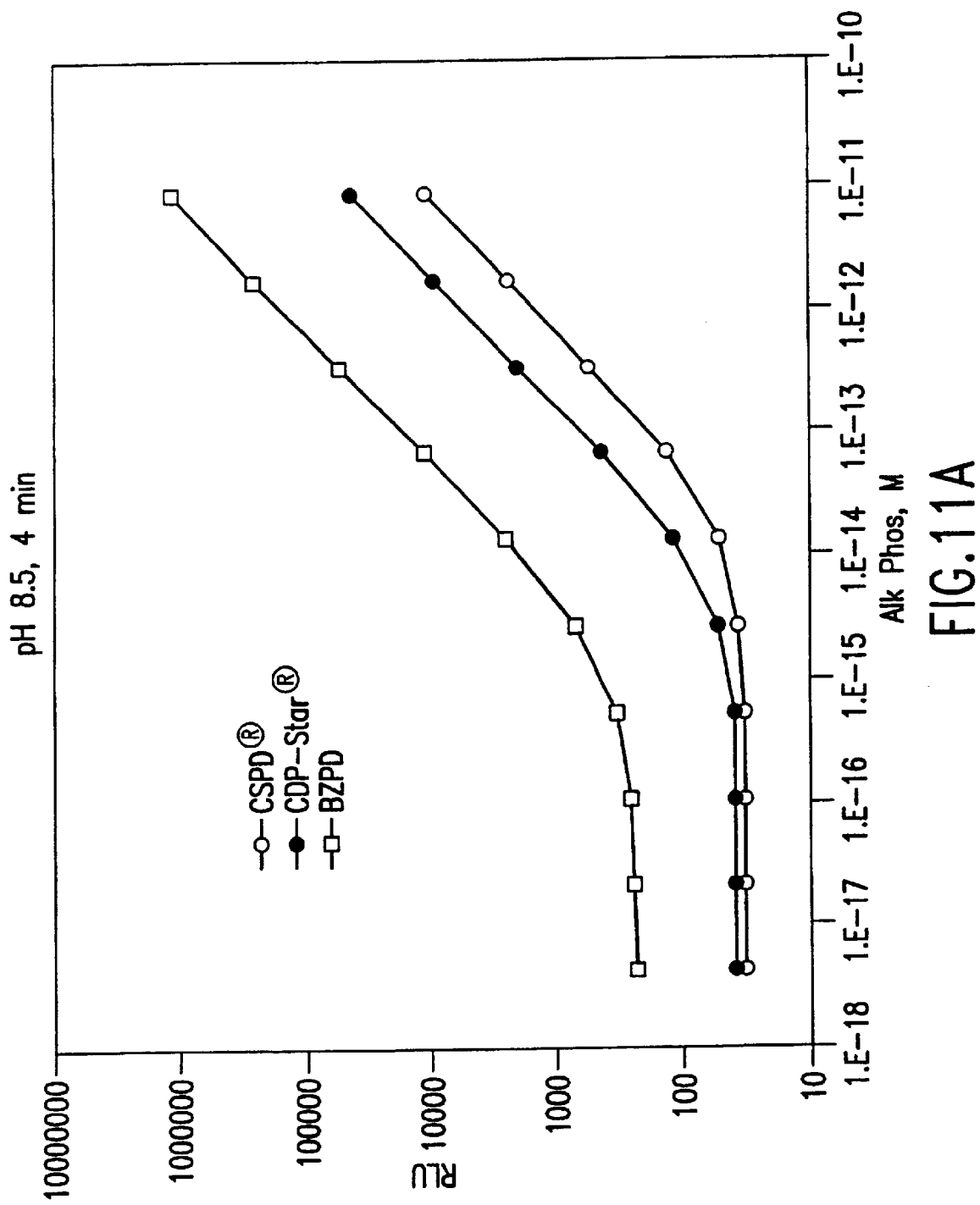
FIG. 11A is a graph showing luminescence (RLU) as a function of alkaline phosphatase concentration for BZPD compared to CSPD® and CDP-Star® at a pH of 8.5 and at a time of 4 min.
Figure 11B:
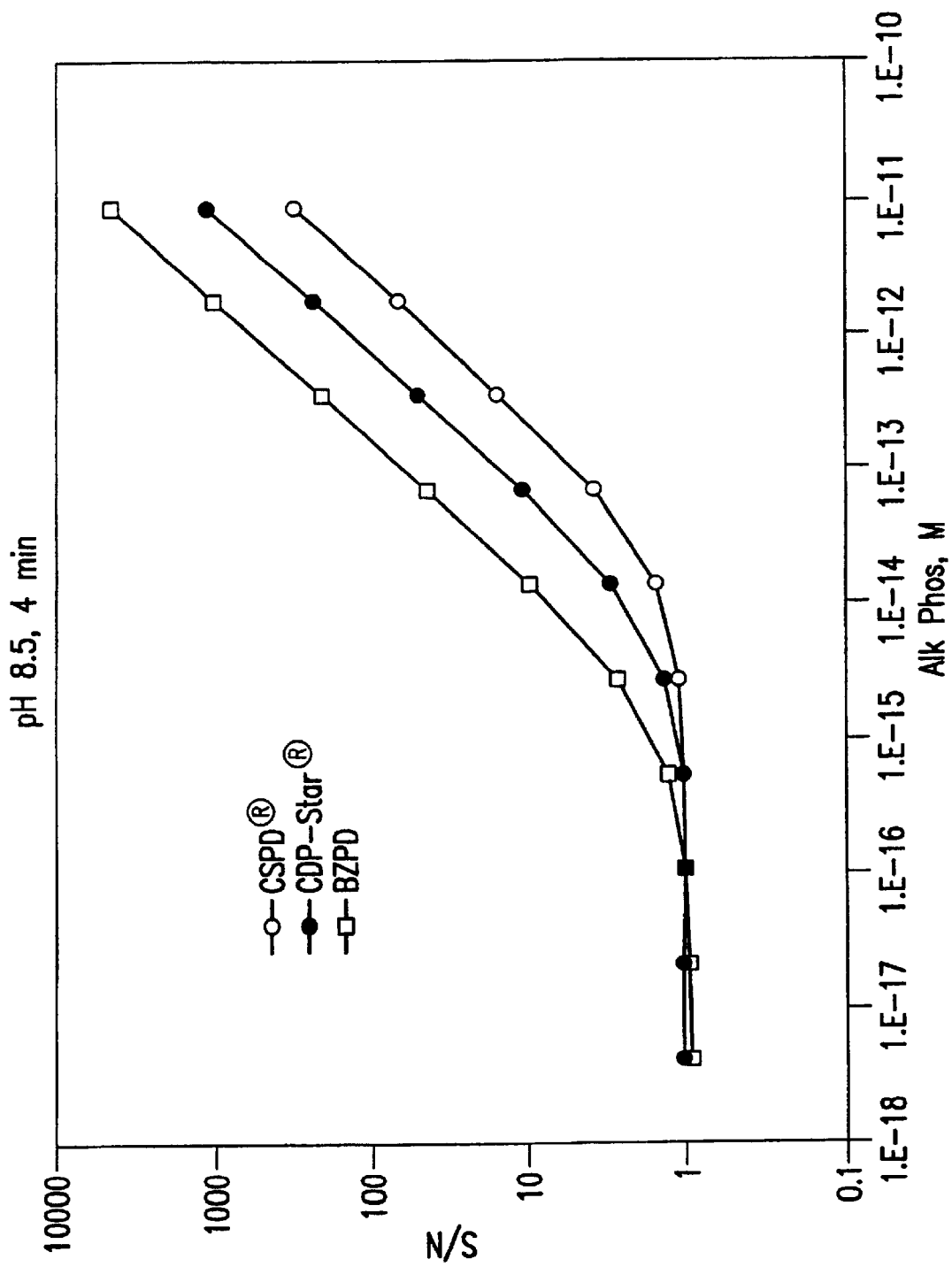
FIG. 11B is a graph showing signal to noise ratio (S/N) as a function of alkaline phosphatase concentration for the luminescence of BZPD compared to CSPD® and CDP-Star® at a pH of 8.5 and at a time of 4 min.
Figure 12A:
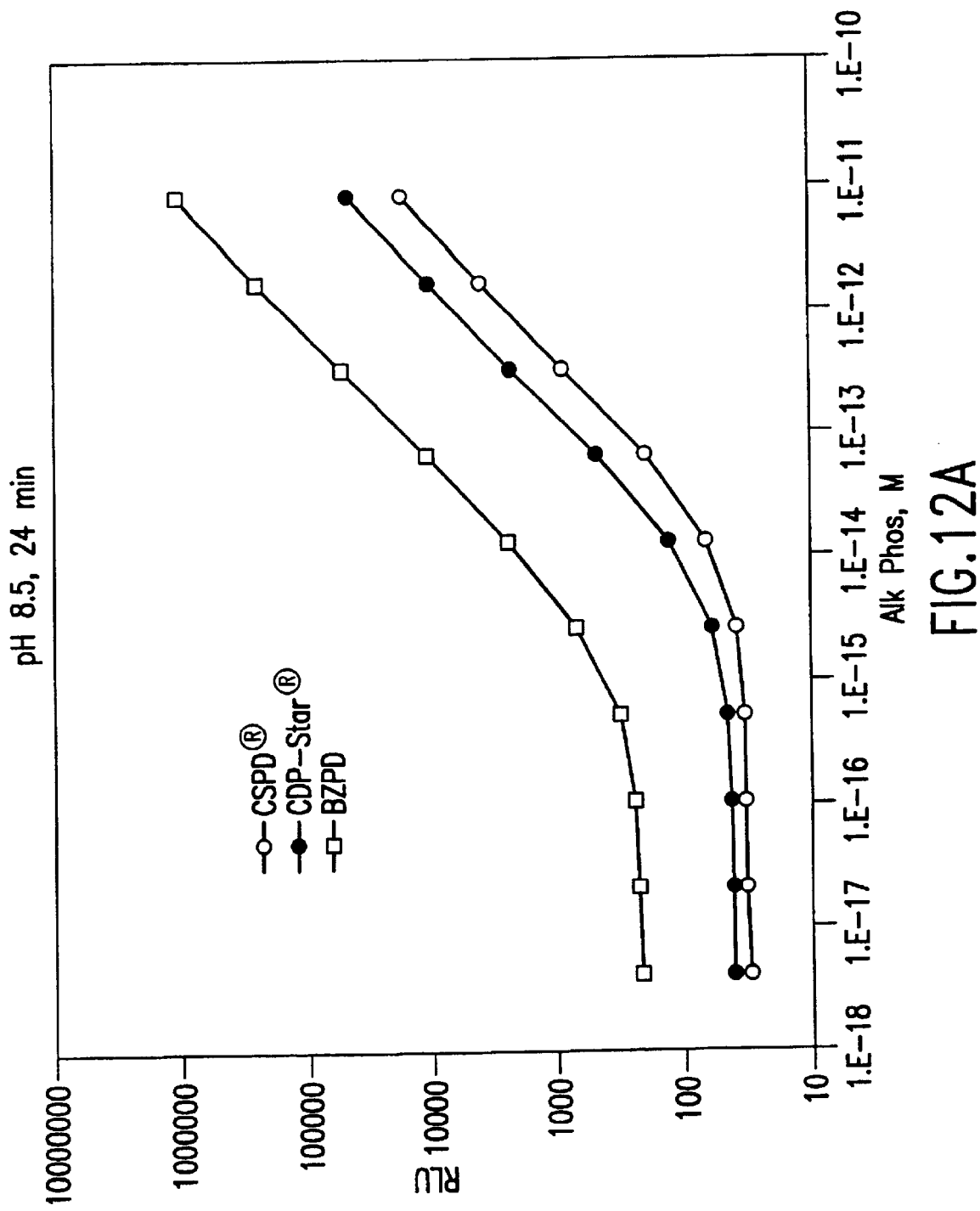
FIG. 12A is a graph showing luminescence (RLU) as a function of alkaline phosphatase concentration for BZPD compared to CSPD® and CDP-Star® at a pH of 8.5 and at a time of 24 min.
Figure 12B:
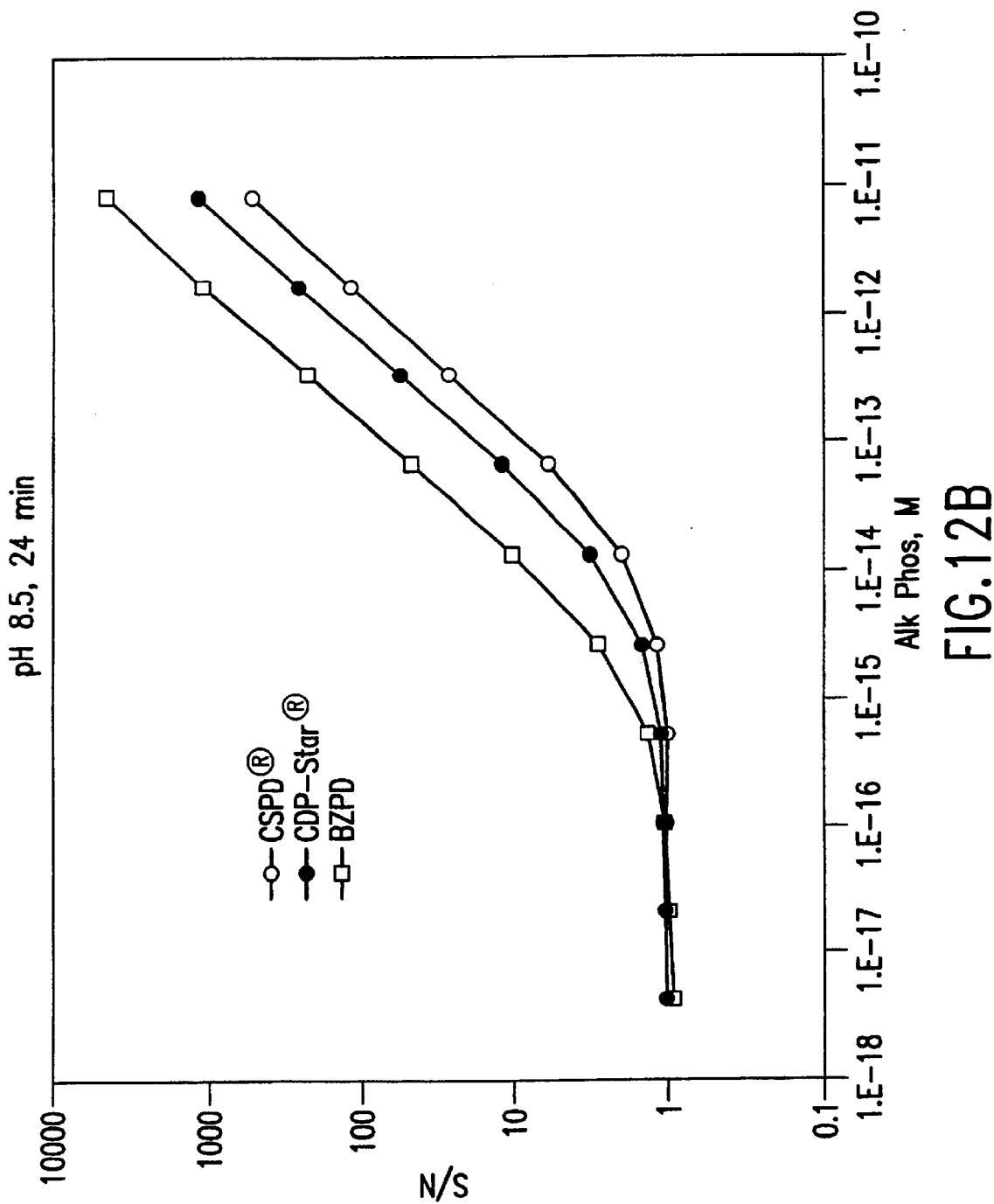
FIG. 12B is a graph showing signal to noise ratio (S/N) as a function of alkaline phosphatase concentration for the luminescence of BZPD compared to CSPD® and CDP-Star® at a pH of 8.5 and at a time of 24 min.

Sensitivity can be an important characteristic of dioxetane detection agents. In FIGS. 11A and 12A, the chemiluminescent signal after four minutes and 24 minutes, respectively, at various concentrations of alkaline phosphatase for BZPD is shown. As clearly shown, BZPD offers superior detection sensitivities (i.e., a greater signal) even at very low concentrations of enzyme ($10^{-17}$ moles or less). As shown in FIGS. 11B and 12B, the S/N ratio of BZPD at low concentrations of alkaline phosphatase is comparable to previously developed dioxetanes whereas at high alkaline phosphatase concentrations the S/N ratio of BZPD is superior. This heightened sensitivity of BZPD can be used to detect very small amounts of material.

Figure 13:
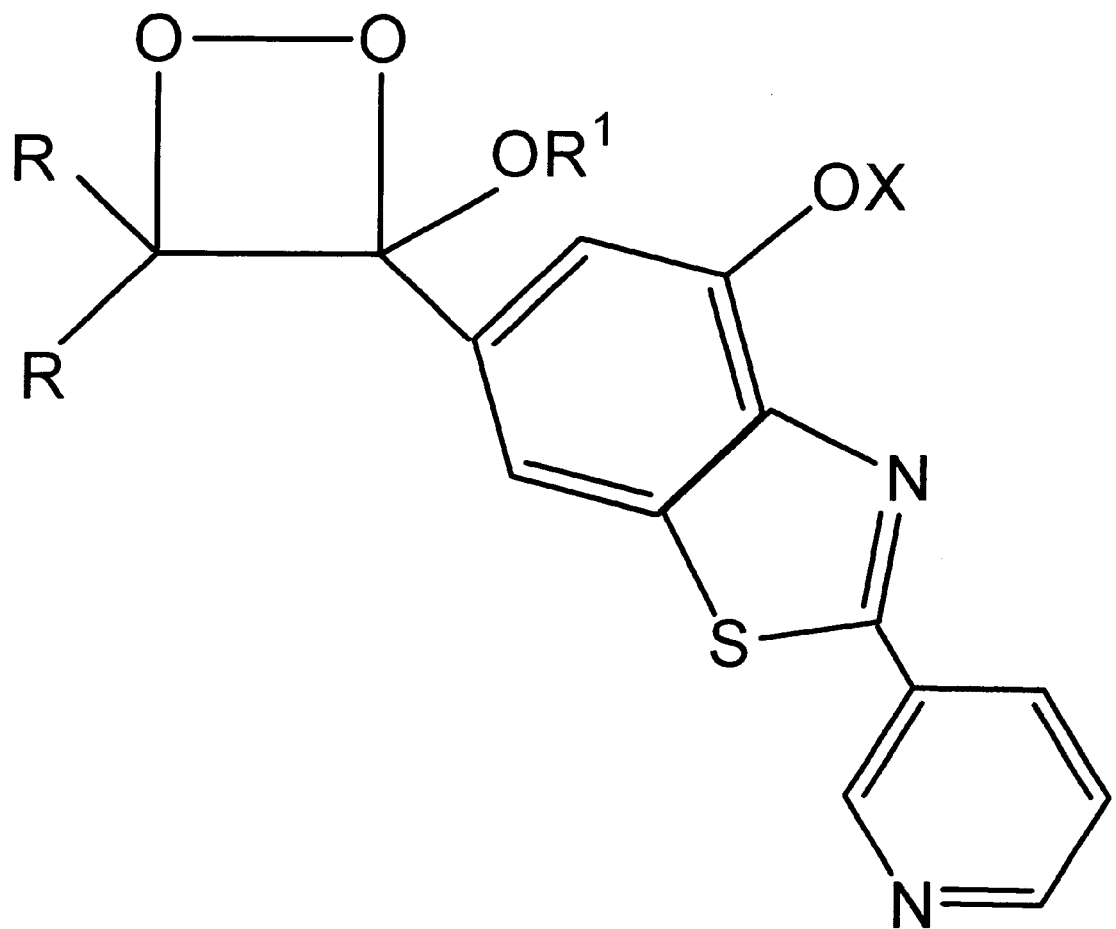
FIG. 13 shows the chemical structure of a 3-pyridyl substituted benzothiazole 1,2-dioxetane according to the invention.
Figure 14:
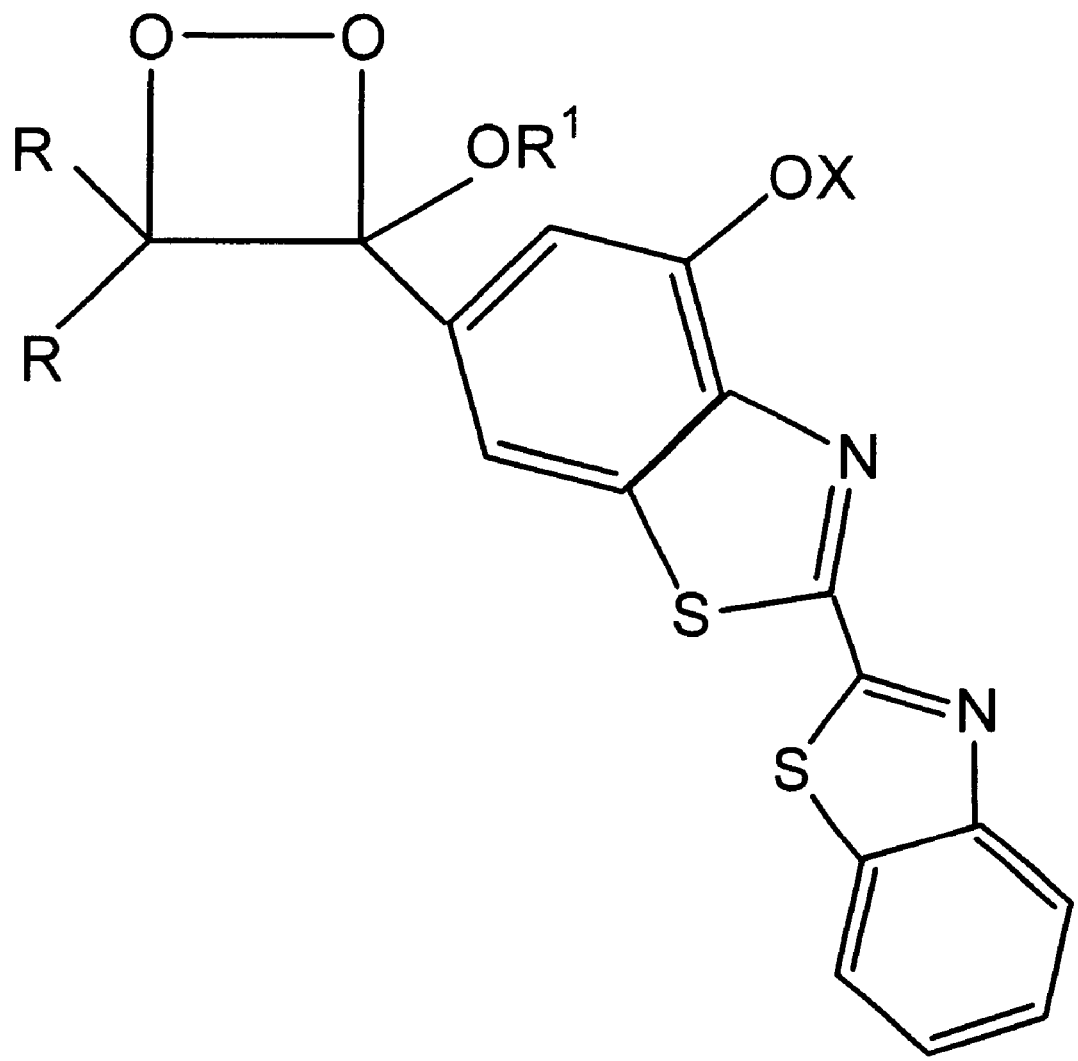
FIG. 14 shows the general structure of a 2-benzothiazolyl substituted benzothiazole dioxetane according to a preferred embodiment of the invention.

FIGS. 13 and 14 illustrate two heteroaryl substituted benzothiazole dioxetanes according to the invention. FIG. 13 shows the general structure of a 3-pyridyl substituted benzothiazole dioxetane according to a preferred embodiment of the invention. FIG. 14 shows the general structure of a 2-benzothiazolyl substituted benzothiazole dioxetane according to a preferred embodiment of the invention. The substituent X in FIGS. 13 and 14 can be a protecting group which can be removed by chemical or enzymatic means.

The emission spectrum for 3-pyridyl-BZPD was measured. The half life ($t_{1/2}$) of the 3-pyridyl-BZPD was found to be about 2 seconds. The maximum emission wavelength ($\lambda_{max}$) of 3-pyridyl-BZPD was found to be about 574 nm. This wavelength is red shifted approximately 24 nm from the maximum emission wavelength of BZPD which is approximately 550 nm.

This red shift observed for 3-pyridyl-BZPD can be used to advantage in various applications. For example, in applications using a CCD camera for detection, the red shift can enhance detection by the CCD. Further, in dual wavelength applications, the red shift of the 3-pyridyl-BZPD can be used to increase sensitivity. For example, in dual wavelength applications where blue light emissions (e.g., $\lambda_{max}$= approximately 470 nm) are used for one event and yellow-orange light (e.g., $\lambda_{max}$=approximately 574 nm) from the decomposition of 3-pyridyl-BZPD is used for another event, greater separation between the two emission spectra can be obtained. Greater separation between the emission spectra can result in greater detection sensitivity. Dual wavelength assays are described in U.S. Pat. No. 4,931,223 which has been incorporated by reference above.

Figure 15:
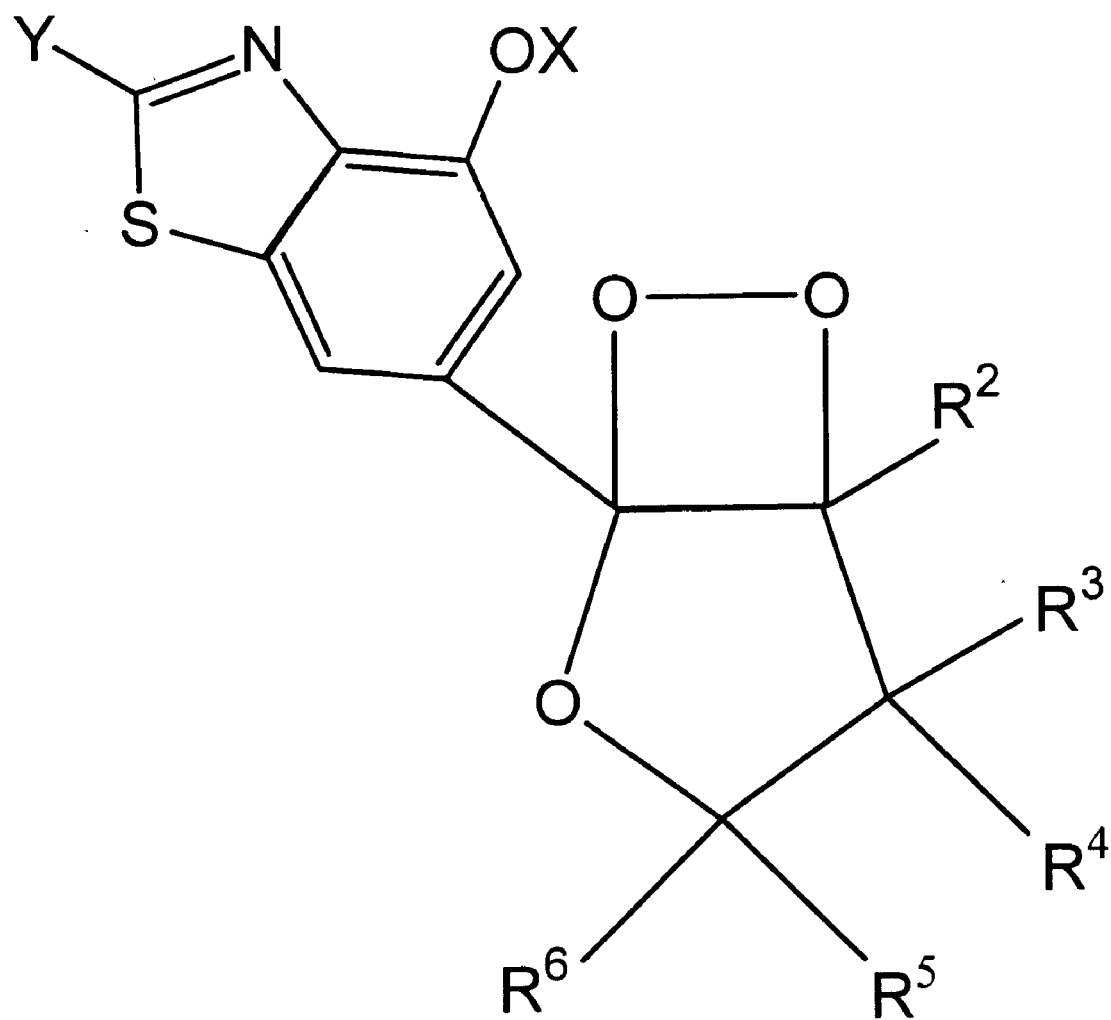
FIG. 15 shows the general structure of a second embodiment of a heteroaryl substituted benzothiazole dioxetane compound according to the invention.

FIG. 15 shows the general structure of a second embodiment of a heteroaryl substituted benzothiazole dioxetane compound according to the invention.

Figure 16:
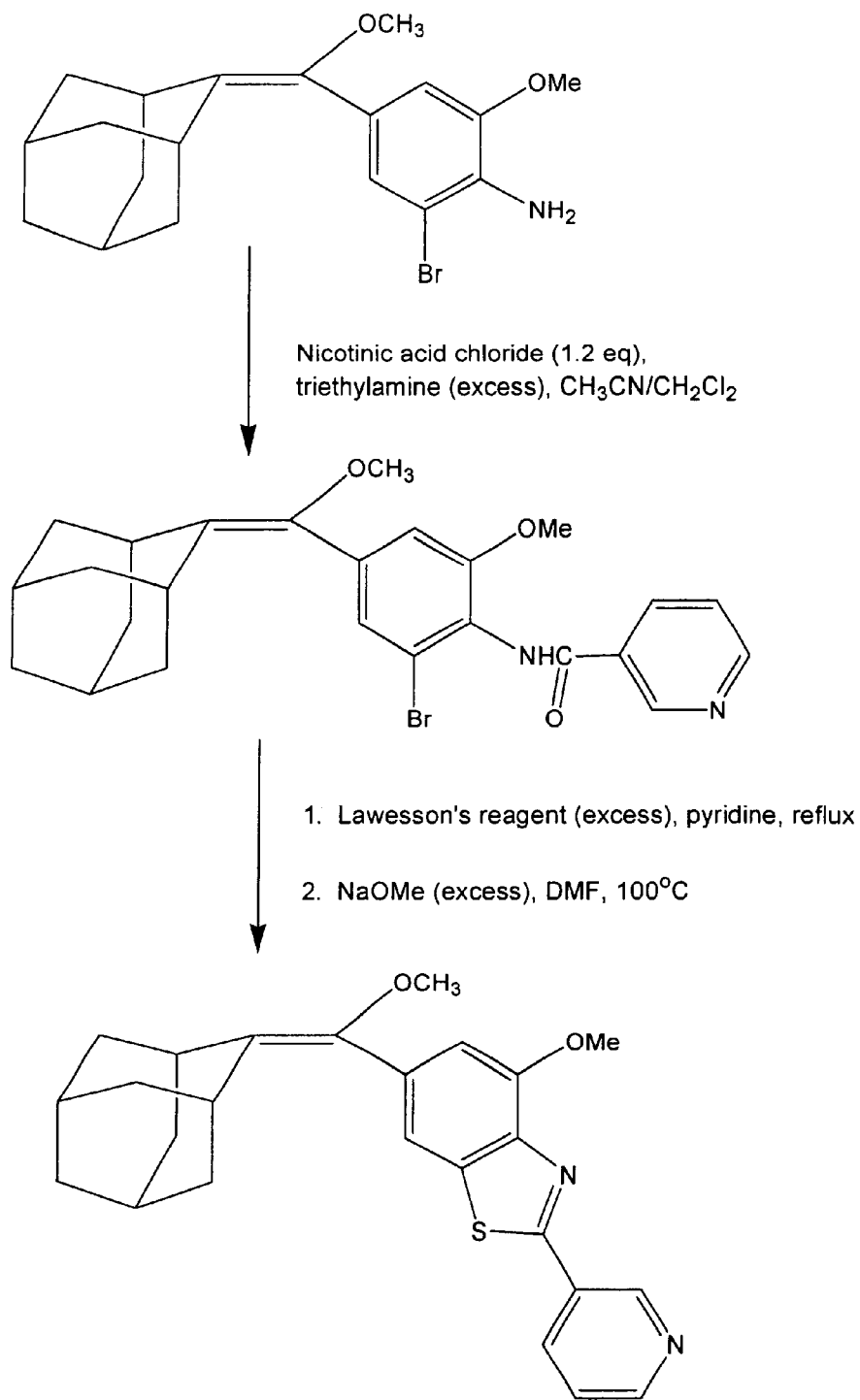
FIG. 16 shows a first route for the synthesis of a 3-pyridyl substituted benzothiazole 1,2-dioxetane.
Figure 17:
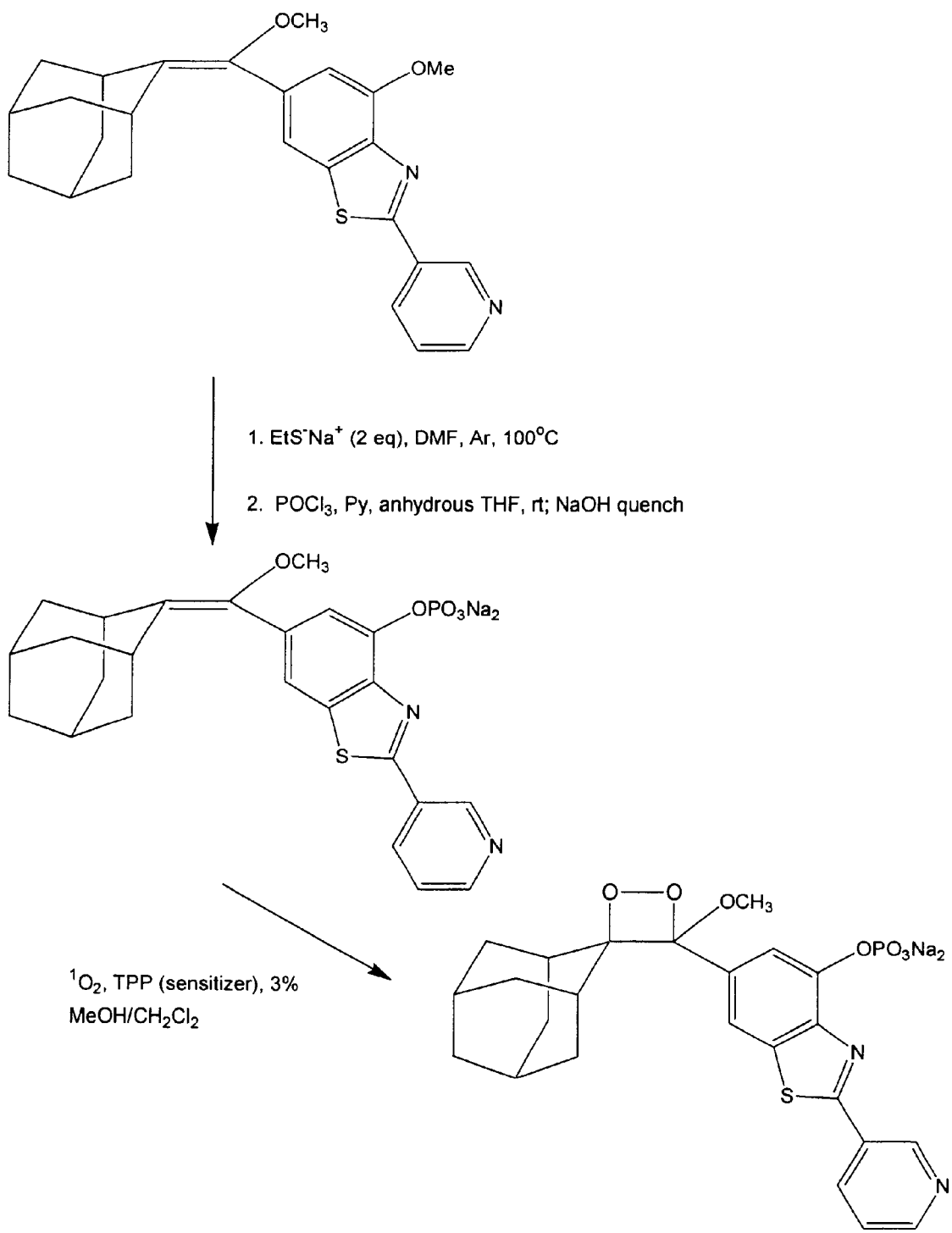
FIG. 17 shows a second route for the synthesis of a 3-pyridyl substituted benzothiazole 1,2-dioxetane.

FIGS. 16 and 17 illustrate a synthesis route for the 3-pyridyl substituted benzothiazole dioxetane shown in FIG. 13.

The 1,2-dioxetanes according to the invention can be used in a method for detecting the presence and amount of an analyte in a sample. Typically, the analyte will cause the dioxetane to decompose and generate light by cleaving the substituent X (as set forth in general Formulae I and II above) from the dioxetane. According to the method of the invention, the sample along with the 1,2-dioxetane of the invention can be incubated and then inspected for the generation of light. If light is detected, the presence of the analyte which removes X is indicated. Further, the amount of light detected can be used to determine the amount of the analyte present in the sample. Typically, the analyte is an enzyme, which is selected to cleave the substituent X on the dioxetane. Upon removal of X, the dioxetane can decompose and generate light. According to the invention, the enzyme can be complexed to a biological moiety of interest.

The methods may be used in conjunction with the enhancement molecules, preferably the onium quaternary polymers and additives, discussed above, and set forth in U.S. Pat. Nos. 5,330,900 and 5,547,836. In preferred embodiments, the light emitted by the decomposition of the 1,2-dioxetane of the invention is detected by a CCD camera.

The chemiluminescent substrates according to the invention can be provided in a kit which includes the 1,2-dioxetanes of the invention either alone, or together with an enzyme or other substance which causes the dioxetane to decompose by removing X. Chemiluminescent enhancers and additives which improve the performance of the enhancers, can also be included in the kits.

The following example is a representative synthesis of benzothiazole dioxetane substrates and their precursors, and should not limit the scope of the claims. First, 4,6-dibromo-o-anisidine was obtained according to the literature: Fuchs, Monatshefte fur Chemie, 36, 130, 1915. A Varian Unity 300 NMR Spectrometer was used. All NMR data is proton($^1$H) NMR.

EXAMPLE 1

2-Benzamido-3,5-dibromoanisole

The 4,5-dibromo-o-anisidine (11.3 g; 40.2 mmol), was dissolved in 75 ml dichloromethane and 6.7 ml pyridine. The mixture was stirred at room temperature under argon. Benzoyl chloride (4.8 ml; 1.03 equivalents) was added dropwise by syringe. The mixture was stirred for 8 hours to obtain an orange-brown suspension. The reaction mixture was then concentrated to one-third volume on the rotary evaporator. The thick slurry was filtered on a Buchner funnel, washing the flask and solid with 50:50 dichloromethane/hexanes. The resulting white solid was then washed liberally with water to remove any pyridine hydrochloride. The solid product was then dried in vacuo to obtain 13.56 grams of the above-titled product. The biphasic filtrate was washed with water in a funnel, separating the organic layer, which was then rotary evaporated to yield a purple brown solid. Trituration with 50:50 dichloromethane/hexanes and recrystallization from minimal ethyl acetate gave a second crop, weighing 1.43 grams. NMR(300 MHz/DMSO-d6) data was as follows: δ 3.81(s, 3H), 7.36(1H), 7.44–7.71(m, 4H), 7.88–8.11(m, 2H) 9.88(s, 1H). IR($CH_2Cl_2$/cm$^{-1}$) data was as follows: 3420, 2980, 2940, 1691, 1585, 1487, 1400, 1041, 875, 837.

EXAMPLE 2

N-(2,4-dibromo-6-methoxy)phenylthiobenzamide

The product of the preceding example (14.4 g; 37.4 mmol) was dissolved in 35 ml dry pyridine with slight warming. Phosphorous pentasulfide (11 g; 49.5 mmol) was added in portions under argon. A thick, light yellow complex formed exothermically. This mixture was stirred for 2 hours in an oil bath at 90° C. to give a thinner, darker yellow suspension. The mixture was then refluxed for 15 minutes and cooled to room temperature. The mixture was treated with 125 ml ethyl acetate to precipitate a gum. Water, 1 ml, was added with swirling to agglomerate the gum prior to decantation of the supernate. The gum was then triturated with 2×25 ml ethyl acetate. The combined organics were rotary evaporated to yield an orange oil which contained pyridine. A 7% solution of sodium hydroxide in water was added to the oil with vigorous stirring for 20 minutes. The solution was filtered to remove insolubles, rinsing with minimal hydroxide solution. The filtrate was then acidified to pH 1 with 3M HCl to precipitate a flocky, light yellow solid, which was dissolved in the minimal quantity of dichloromethane. The organic layer was separated and rotary evaporated to yield 12.6 grams of the above-titled product as a lemon-yellow solid. Analytical samples could be obtained by recrystallization from ethanol to yield a one-spot material on TLC (Kieselgel 60-dichloromethane; Rf=0.56). NMR(300 MHz/DMSO-d6) data was as follows: δ 3.81(s, 3H), 7.40–7.59(m, 6H), 7.90–7.93(m, 2H), 11.36(s, 1H). IR($CHCl_3$/cm$^{-1}$) data was as follows: 3380, 2990, 1584, 1490, 1400, 1345, 1040, 878, 838, 695.

EXAMPLE 3

2-Phenyl-4-methoxy-6-bromobenzothiazole

The thioamide from the preceding example (12.6 g; 31.4 mmol) was warmed in 30 ml of methanol. The suspension was swirled during the addition of 7.35 ml of 4.3 M sodium methoxide in methanol (31.6 mmol). During the addition, the solid dissolved and the yellow color faded to light amber. Rotary evaporation of the solvent and pumping in vacuo gave an amber, glassy solid which coated the glass. This thioamide salt was kept under argon during the addition of 20 ml of N-methylpyrrolidone. The flask was capped with a septum and connected to a bubbler as it was placed in an oil bath at 110–120° C. Upon stirring for 30 minutes, a solid developed as the color became green-brown. The flask was then cooled toward room temperature before 100 ml of water was added to produce an off-white solid. The mixture was filtered, and the solid washed liberally with water. After drying in vacuo, the solid was recrystallized from 50:50 ethyl acetate:hexanes to yield 7.05 grams of white, hair-like needles. TLC showed the blue fluorescent product spot at Rf=0.47, while a trace UV absorbing impurity was present at a higher Rf (Kieselgel 60-dichloromethane). The impurity could be removed by silica gel chromatography to obtain an analytical sample. NMR and IR data were consistent with the structure of the above-titled product. In particular, NMR (300 MHz/CDCl$_3$) data was as follows: δ 4.10(s, 3H), 7.07(d, 1H), 7.49–7.52(m, 3H), 7.66(d, 1H), 8.11–8.14(m, 2H), and IR($CHCl_3$/cm$^{-1}$) data was as follows: 3003, 2940, 1590, 1562, 1517, 1440, 1400, 1387, 1322, 1260, 1055, 978, 830, 690.

EXAMPLE 4

2-Phenyl-4-methoxy-6-formylbenzothiazole

The chromatographed product from the preceding example (3 g; 9.37 mmol) was dissolved in 70 ml of dry THF under argon. In another flask, 60 ml dry THF was cooled and stirred at −78° under argon. To this flask, 5.6 ml of 2.5 M n-Butyllithium (14.1 mmol) was added by syringe. The solution of bromobenzothiazole starting material was then added dropwise under argon from an addition funnel over 25 minutes. THF, 7 ml, was used to rinse the funnel at the conclusion of the addition. The red-brown solution was stirred for another 10 minutes at low temperature. Dry DMF, 1.8 ml, was then added dropwise by syringe. After 10 minutes, the solution was slowly warmed to room temperature over 1 hour. The reaction was quenched by the rapid addition of 20 ml of 1 M aqueous ammonium chloride solution. The THF was removed on the rotovap, and the product was partitioned between ethyl acetate and the remaining water. The ethyl acetate layer was washed four times with water to remove any DMF. The organics were dried over sodium sulfate and the solvent removed to yield a semi-solid paste. This was triturated with 20 ml of 20% dichloromethane in hexanes to yield a dry solid after decantation and pumping in vacuo. The resulting peach-colored product weighed 1.81 g TLC and showed essentially one spot at an Rf value of 0.62 (Kieselgel 60–10% ethyl acetate/hexanes). Spectral data for a similarly obtained product were identical and consistent with that expected for the above-titled compound. NMR(300 MHz/CDCl$_3$) data was: δ4.18(s, 3H), 7.48–7.56(m, 4H), 8.04(d, 1H), 8.17–8.20(m, 2H), 10.08(s, 1H). IR(CHCl$_3$/cm$^{-1}$) data was: 3010, 2840, 2740, 1695, 1595, 1572, 1480, 1470, 1395, 1290, 1270, 1145, 1057, 983, 850, 690.

EXAMPLE 5

2-Phenyl-4-methoxy-6-formylbenzothiazole Dimethyl Acetal

Under argon, 1.8 grams of the aldehyde from the previous example (6.7 mmol) was treated with 11 ml dichloromethane, 0.9 ml of trimethylorthoformate, and 0.7 ml of anhydrous methanol. The suspension was stirred as 105 mg of toluenesulfonic acid monohydrate was added all at once. The flask was closed with a septum after purging it with argon. The solid soon dissolved to give a yellow-orange solution. Stirring was continued overnight at room temperature. The reaction mixture was neutralized with excess triethylamine (0.15 ml) using a syringe. The mixture was stripped of all volatiles, dissolved in minimal dichloromethane, and plug-chromatographed on a 2 cm×1.5 inch column of Alumina. The eluant was rotary evaporated and pumped to an oil which slowly solidified. A sample was taken for immediate IR analysis, which showed the absence of any carbonyl absorption. This indicated that acetal formation was complete, and the crude product was used immediately for the next reaction. IR(CH$_2$Cl$_2$/cm$^{-1}$) data was as follows: 2940, 2840, 1602, 1580, 1468, 1410, 1355, 1198, 1155, 1060, 996, 837.

EXAMPLE 6

Diethyl-1-methoxy-1-(2-phenyl-4-methoxybenzothiazol-6-yl)methanephosphonate

The crude product obtained in the previous step was dissolved in 11 ml of sieve-dried dichloromethane and 1.5 ml of triethylphosphite under argon. The flask was sealed with a septum, and the stirred solution was cooled to −78° C. in a dry ice/acetone bath. The pressure was equilibrated at this temperature with an argon balloon. The mixture, which became a suspension, was then treated dropwise with 1.0 ml of borontrifluoride etherate. The suspended solid dissolved as the contents were slowly warmed to about −20° C. The solution was stored in the refrigerator for one hour and then slowly warmed to room temperature for an overnight stirring period. In the morning, 0.7 grams of solid sodium bicarbonate was added, followed by 15 ml of saturated, aqueous sodium bicarbonate solution. The biphase was stirred vigorously to expel carbon dioxide. Water was added as necessary over 3 hours to dissolve any inorganics. The dichloromethane layer was separated, and the aqueous layer was back-extracted with 15 ml of the same solvent. The combined organics were subjected to TLC to show a single, UV/blue fluorescent spot at approximately Rf=0.15, tailing back to the origin (Kieselgel 60-ethyl acetate). The solution was evaporated and vacuum pumped at 40° C. The viscous yellow oil was then dissolved in a minimal amount of 50/50 dichloromethane/ethyl acetate and passed over a very short plug of silica gel. The eluant was stripped and chased several times with a mixture of dichloromethane/hexanes. The oily product weighed 2.7 grams. NMR and IR spectroscopy showed a substantially pure product, but the presence of moisture was indicated. NMR(300 MHz/CDCl$_3$) data was: δ 1.21–1.36(m, 6H), 3.46(s, 3H), 3.93–4.21(m, 7H), 4.59–4.64(d, 1H), 7.07(s, 1H), 7.47–7.52(m, 3H), 7.57(s, 1H), 8.11–8.14(m, 2H). IR(CH$_2$Cl$_2$/cm$^{-1}$) data was: 3660 & 3460(H$_2$O), 2980, 2935, 2860, 1597, 1570, 1510, 1480, 1460, 1445, 1408, 1342, 1245–1285(br), 1100, 1040(br), 965(br), 865, 840, 610.

EXAMPLE 7

6-(Methoxytricyclo[3.3.1.$^{3,7}$]dec-2-ylidenemethyl-2-phenyl-4-methoxybenzothiazole The pumped phosphonate ester from the previous step (2.7 g; 6.4 mmol) was dissolved in 25 ml of dry THF under argon. The solution was cooled to −78° C. with stirring in a flask outfitted with a septum and an argon balloon. The solution was treated dropwise with enough 2.5 M n-BuLi in hexanes to achieve a just permanent, red-purple color. In this process, all moisture and protic impurities have been titrated. Subsequently 2.7 ml of the same n-BuLi solution (6.75 mmol) were added dropwise to yield a deep burgundy solution. After 10 minutes stirring at low temperature, 2-adamantanone (0.95 grams, 6.33 mmol) was added as a solid under strong argon flow to exclude moisture. The solid dissolved over 10 minutes. The solution was then allowed to warm slowly to room temperature. A reflux condenser was attached while maintaining an argon atmosphere. The mixture was refluxed for 1.5 hours to obtain a light orange solution. THF was then stripped on the rotary evaporator taking care to avoid foaming. The product was partitioned between 25 ml ethyl acetate and 50 ml 1:1 saturated sodium bicarbonate/water. The organic layer was then washed with 25 ml of water. The organic layer was dried over sodium sulfate and stripped to yield a light yellow gum. The gum was plug-chromatographed on a short column of silica gel, eluting with dichloromethane to remove trace polar contaminants. The appropriate fractions were pumped and chased with dichloromethane-hexanes. The pumped product, weighing 2.14 grams, became a semi-solid upon storage in the freezer. IR spectroscopy revealed a small 2-adamantanone carbonyl band, indicating minor contamination which would be eliminated in the next step. IR(CH$_2$Cl$_2$/cm$^{-1}$) data was as follows: 2920, 2850, 1597, 1567, 1450, 1402, 1330, 1320, 1310, 1252, 1165, 1100, 1057, 978, 865, 640, 620. Trace AD=O at 1720 and 1710.

EXAMPLE 8

6-(Methoxytricyclo[3.3.1.1$^{3,7}$]dec-2-ylidenemethyl)-2-phenyl-4-hydroxybenzothiazole A sodium ethanethiolate solution in DMF was made from 60% sodium hydride and ethanethiol: 240 mg of 60% sodium hydride (6 mmol) was washed three times with hexanes under an argon atmosphere, removing the mineral oil. DMF, 11 ml, was added. The resulting suspension was cooled to 0° C. with stirring for the dropwise addition of ethanethiol (0.45 ml, 6 mmol). After hydrogen evolution ceased, the solution was warmed to room temperature and delivered by pipette to 1.64 grams of methoxy[2-phenyl-4-methoxy(benzothiazol-6-yl)methylidene adamantane in a separate flask (3.9 mmol) under argon. The resulting solution was stirred in an oil bath at 130° C. After one hour, the solution was deep orange and contained suspended solid. The reaction mixture was cooled and partitioned between 50 ml each of 1 M ammonium chloride and 75% ethyl acetate/hexanes. The organic layer was washed 3 times with 25 ml of water. The combined aqueous layers were back-extracted with the same solvent mixture, which was then washed several times with water. The combined organics were dried over sodium sulfate. TLC (Kieselgel 60-dichloromethane) showed product at Rf=0.23, but also starting material at Rf=0.39. Column chromatography (silica gel: 50% dichloromethane-hexanes to pure dichloromethane) allowed one pure fraction of the lower Rf product to be isolated. Repeat chromatography of the mixed fractions allowed additional product to be isolated. After stripping the solvents, a total of 245 mg of the above-entitled product was obtained. NMR(300 MHz/$CD_2Cl_2$) data was as follows: $\delta$1.74–2.07(m, 14H), 2.71(s, 1H), 3.26 (s, 1H), 3.32(s, 3H), 6.76(s, 1H), 6.94(d, 1H), 7.38(d, 1H), 7.44–759(m, 3H), 7.99–8.16(m, 2H). IR($CH_2Cl_2/cm^{-1}$) data was: 3520, 2910, 2850, 1612, 1575, 1480, 1445, 1302, 1284, 1175, 1080, 980, 860.

EXAMPLE 9

Disodium 6-(methoxytricyclo [$3.3.1.1^{3,7}$]dec-2-ylidenemethyl)-2-phenylbenzothiazolyl-4-phosphate Molecular sieve-dried pyridine, 4.0 ml, was placed in a flask under argon. The flask was outfitted with a magnetic stir bar and placed in an ice bath. Distilled phosphorus oxychloride, 0.112 ml (1.2 mmol), was added dropwise by syringe. In another flask, 245 mg of the hydroxybenzothiazole derivative from the previous example was dissolved in 15 ml of anhydrous THF under argon. The THF solution was then added slowly and dropwise to the stirred solution of phosphorylating agent. During the addition, a precipitate developed. At the end of the addition, the flask and syringe were rinsed with 2 ml of THF which was also added slowly to the reaction flask. The reaction mixture was then warmed to room temperature and stirred for three hours. A cotton-tipped needle on a 20 ml syringe was used to draw up the supernate, leaving the pyridine hydrochloride behind. This supernate was added dropwise to a solution of 15 ml 0.5 M sodium hydroxide, which had been diluted to a volume of 75 ml with water, while being stirred at ice-bath temperature. The slightly cloudy solution cleared upon warming to room temperature. The solution was carefully pumped to remove THF and the volume adjusted to 110 ml with 5.0 ml acetonitrile and water. This solution was injected in two portions onto a Polymer Laboratories 2 inch polystyrene reverse-phase HPLC column. A gradient of 5% to 10% acetonitrile was used to allow separation of the major peak absorbing at 270 nm. This gradient will require optimization for any specific equipment. The appropriate fractions were pooled and lyophilized to obtain 294 mg of a light yellow solid. Spectral data were in concert with the above-titled structure. An analytical HPLC chromatogram on a similar support, using an acetonitrile gradient against 0.1% aqueous sodium bicarbonate, showed a single product eluting at 13.2 minutes (approximately 50% acetonitrile). The NMR(300 MHz/$D_2O$) data was: $\delta$ 1.38–2.02(m, 14H), 2.51(s, 1H), 3.00(s, 1H), 3.24(s, 3H), 7.26–7.53(m, 5H), 7.75–8.04(m, 2H).

EXAMPLE 10

Disodium 6-(4-methoxyspiro-[1,2-dioxetane-3,2'-tricyclo[$3.3.1.1^{3,7}$]decan]-4-yl)2-phenylbenzothiazolyl-4-phosphate In a tube was placed 285 milligrams of the enol ether phosphate from the previous step. The solid was wet down with 1.0 ml of methanol and then dissolved by adding 25 ml of dichloromethane. The solution was then treated with 0.5 ml of a solution of 5, 10, 15, 20-tetraphenyl-21H, 23H-porphine (2 mg/ml in $CHCl_3$). The contents of the tube were cooled to 0° C., while the solution was sparged with oxygen gas. After 5 minutes, while continuing to bubble oxygen through the solution, the tube was irradiated with light from a cooled, 400 watt sodium vapor lamp while maintaining the temperature at 5° C. A 5 mil thick piece of Kapton polyimide film, placed between the lamp and the tube, filtered out unwanted UV radiation. The irradiation was continued for 17 minutes. Analytical HPLC [0.1% $NaHCO_3$ ($H_2O$)-acetonitrile gradient] showed that the conversion of the starting material, eluting at 13.2 minutes, to the 1,2-dioxetane, which eluted at 12.94 minutes, was substantially complete. The reaction mixture was stripped of solvents to give a red gum. Acetonitrile, 5 ml, and 0.05 M aqueous sodium hydroxide, 20 ml, were added with swirling and occasional cooling to dissolve the gum. DI water was then added to give a total volume of 70 ml. This solution was filtered through highly retentive filter paper, rinsing carefully with water in small portions, to give a filtrate volume of 110 ml. This solution was injected in two portions onto a Polymer Laboratories 1 inch polystyrene reverse-phase HPLC column. A gradient of 5% to 100% acetonitrile (against water) was used to allow separation of the major peak absorbing at 270 nm. This gradient will require optimization for any specific equipment. An analytical HPLC chromatogram of the combined product fractions on a similar support, using an acetonitrile gradient against 0.1% aqueous sodium bicarbonate, showed a single product eluting at 12.96 minutes (approximately 50% acetonitrile). The appropriate fractions were pooled and lyophillized to obtain 287 mg of a light yellow solid. The product 1,2-dioxetane produced green light at 558 nm when triggered with alkaline phosphatase in an aqueous buffer at pH 8.5. UV: 213, 260.5, and 304 nm in 50/50 $CH_3CN/H_2O$.

EXAMPLE 11

2-Methoxy-4,6-dibromophenylisothiocyanate

In a flask under argon were placed 19.75 grams of 4,6-dibromo-o-anisidine (70 mmol) and 20 grams of solid bicarbonate. A large, heavy-duty magnetic stir bar was added, followed by 120 ml acetonitrile and 50 ml dichloromethane. The suspension was stirred at 0° C. as 6.0 ml of thiophosgene was added rapidly by syringe. A thick precipitate developed immediately. This was stirred vigorously as the contents of the flask were slowly warmed to room temperature. The carbon dioxide generated was led to a bubbler with a needle vent. The mixture thinned slightly as it warmed and was more easily stirred. Vigorous stirring was continued for two hours. The suspension was then recooled to 0° C. The solid was filtered off on a Buchner funnel, rinsing the flask and transferring any remaining solid with 30 ml of cold acetonitrile. The filtrate was rotary evaporated to a solid containing areas of orange discoloration. This solid was triturated with hexanes, pumped dry, and transferred to the Buchner funnel containing the white, original filter cake. This solid was washed with 5×100 ml portions of a 0.5 M aqueous solution of NaH$_2$PO$_4$ in order to neutralize the inorganic bicarbonate present (carbon dioxide was released). The solid was broken up during each rinse. The white product was then washed liberally with water and dried in vacuo. The dry product weighed 21.8 grams. Analytical data obtained from a similarly synthesized product were in agreement with the above-titled structure. NMR(300 MHz/CDCl$_3$) data was: δ 3.92(s, 3H), 6.98(d, 1H), 7.31 (d, 1H). IR(CH$_2$Cl$_2$/cm$^{-1}$) data was: 3020, 2970, 2940, 2030(br), 1575, 1555, 1470, 1400, 1040, 935, 870, 840.

EXAMPLE 12

2-Phenyl-4-methoxy-6-bromobenzothiazole[One Pot Method]

About 15.5 grams of the isothiocyanate from the preceding example (48 mmol) was dissolved in 50 ml of dry THF under argon. The solution was cooled to 0° C. with stirring in an ice bath. A solution of phenylmagnesium bromide (Aldrich, 1.0 M in THF), 50 ml (50 mmol), was added by syringe in a thin stream. After stirring in the cold for 10 minutes, the solution was slowly warmed to room temperature. At this points a precipitate began to appear as a minor exotherm occurred. The light orange-brown suspension became thicker over 2 hours. The solvent was removed by rotary evaporation at 30° C. to obtain a moist, peach-colored solid coating the glass. This material was protected from air as 50 ml of sieve-dried DMF was added. The solid dissolved with a slight exotherm. The flask was placed in an oil bath at 125° C. Over 45 minutes, any residual THF was allowed to distill from the flask using a short path distillation head. The mixture darkened during this time, and a suspended solid was produced. Upon cooling to room temperature, the contents of the flask solidified. Aqueous 1 M HCl, 100 ml was added, breaking up the solid. Water, 100 ml, was added subsequently. The mixture was macerated to remove any coordinated magnesium ion. The mixture was then filtered and washed well with water. The moist solid was taken up in 2×250 ml warm ethyl acetate, separating the supernate from insoluble flock. The combined organics were dried over sodium sulfate and stripped to give 13.27 grams of a light brown solid. TLC showed a major blue fluorescent product spot at Rf=0.47, while a trace UV absorbing impurity was present at a higher Rf (Kieselgel 60-dichloromethane). A small, colored origin spot was removed by plug chromatography over silica gel (dichloromethane). Combining the appropriate fractions gave 12.29 grams of the product, essentially identical to that of Example 3, but still containing a trace amount of the higher Rf impurity. The reaction of this example may also be acidified and worked up after the phenyl magnesium bromide has reacted with the isothiocyanate to obtain the thioamide product of Example 2.

The following were also synthesized according to the general synthetic methodology described above. One of skill in the art may easily invoke minor modifications as necessary. Any other route to the benzothiazole system may be employed as well.

EXAMPLE 13

2-(p-benzyloxybenzamido)-3,5-dibromoanisole
NMR(300 MHz/DMS0-d6):δ 3.79(s, 3H), 5.21(2H), 7.11–7.14(d, 2H), 7.34–7.52(m, 7H), 7.93–7.96(d, 2H), 9.70 (s, 1H).

EXAMPLE 14

N-(2,4-dibromo-6-methoxy)-p-benzyloxyphenylthiobenzamide
NMR(300 MHz/DMS0-d6):δ 3.80(s, 3H), 5.22(2H), 7.08–7.11(d, 2H), 7.32–7.55(m, 7H), 7.95–7.98(d, 2H), 11.12(s, 1H).

EXAMPLE 15

2-(p-benzyloxy)phenyl-4-methoxy-6-bromobenzothiazole

NMR(300 MHz/DMS0-d6):δ 4.00(s, 3H), 5.21(2H), 7.17–7.22(m, 3H), 7.34–7.50(m, 5H), 7.93–8.01(m, 3H).

EXAMPLE 16

2-(p-benzyloxy)phenyl-4-methoxy-6-formylbenzothiazole

NMR(300 MHz/DMS0-d6):δ 4.05(s, 3H), 5.23(2H), 7.20–7.23(d, 2H), 7.33–7.50(m, 6H), 8.05–8.08(d, 2H), 8.31–8.32(d, 1H), 10.04(s, 1H).

EXAMPLE 17

2-(p-benzyloxy)phenyl-4-methoxy-6-formylbenzothiazole Dimethyl Acetal

IR(CHCl$_3$/cm$^{-1}$): 3000, 2940, 2840, 1611, 1580, 1530, 1490, 1470, 1355, 1180, 1155, 1060, 1020,980,838,700.

EXAMPLE 18

Diethyl-1-methoxy-1-[2-(p-benzyloxy)phenyl-4-methoxybenzothiazol-6-yl]methanephosphonate NMR(300 MHz/CDCl$_3$):δ 1.19–1.37(m, 6H), 3.43(s, 3H), 3.86–4.18(m, 7H), 4.51–4.75(m, 1H), 5.12(s, 2H), 7.02–7.03(m, 2H), 7.30–7.52(m, 7H), 8.02–8.06(m, 2H).

Example 19

6-(Methoxytricyclo[3.3.1.1$^{3,7}$]dec-2-ylidenemethyl)-2-(p-benzyloxy)phenyl-4-methoxybenzothiazole NMR(300 MHz/CDCl$_3$):δ1.78–2.1(m, 14H), 2.74(s, 1H), 3.30(s, 1H), 3.35(s, 3H), 4.06(s, 3H), 5.12(s, 2H), 6.85–6.96 (m, 1H), 6.99–7.12(m, 2H), 7.29–7.50(m, 6H), 7.99–8.14 (m, 2H).

TABLE 1

| Half-life of Dephosphorylated dioxetanes pH 10. | |
|---|---|
| Dioxetane | t ½, sec |
| BZPD | 2.3 |
| CSPD ® | 57.6 |
| CDP-Star ® Plus Sapphire-II ™ | 96 |
| BZPD | 54.9 |
| CSPD ® | 228 |
| CDP-Star ® | 420 |

What is claimed is:
1. A 1,2-dioxetane compound capable of producing light energy when decomposed, represented by the formula:

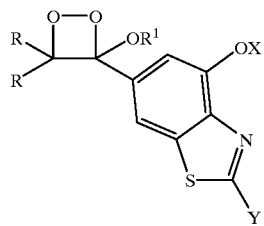

wherein R may independently be any branched alkyl or cycloalkyl group which provides stabilization for the dioxetane or wherein both R groups together form a cycloalkyl or polycycloalkyl moiety Spiro bound to the dioxetane ring; wherein each R group or the Spiro bound moiety may be unsubstituted or substituted with one or more electron-withdrawing groups or electron-donating groups; wherein $R^1$ is an aryl group or an alkyl group of 1–20 carbon atoms which may be optionally substituted with 1 or more halogen atoms; wherein Y is a heteroaryl group; and wherein X is a protecting group which can be removed by non-enzymatic chemical or enzymatic means.

2. The compound of claim 1, wherein X is a phosphate group, $R^1$ is a methyl group and wherein both R groups together form a spiro bound adamantyl group.

3. The compound of claim 1, wherein the heteroaryl group Y is selected from the group consisting of pyridyl, benzothiazolyl, benzoxazolyl, benzofuranyl, benzothienyl, thiazolyl, isoxazolyl, isothiazolyl, quinolinyl, and pyrimidinyl.

4. The compound of claim 3, wherein the heteroaryl group Y is a pyridyl selected from the group consisting of 2-pyridyl, 3-pyridyl, and 4-pyridyl.

5. The compound of claim 3, wherein the heteroaryl group Y is 2-benzothiazolyl.

6. The compound of claim 3, wherein the heteroaryl group Y is a thiazolyl selected from the group consisting of 2-thiazolyl, 4-thiazolyl, and 5-thiazolyl.

7. The compound of claim 3, wherein the heteroaryl group Y is an isoxazolyl selected from the group consisting of 3-isoxazolyl, 4-isoxazolyl, and 5-isoxazolyl.

8. The compound of claim 3, wherein the heteroaryl group Y is an isothiazolyl selected from the group consisting of 3-isothiazolyl, 4-isothiazolyl, and 5-isothiazolyl.

9. The compound of claim 1, wherein the heteroaryl group is substituted with one or more electron active groups.

10. A kit for detecting the presence of an analyte in a sample comprising:
the 1,2-dioxetane compound of claim 1; and
a substance which, in the presence of the dioxetane, causes the dioxetane to decompose and generate chemiluminescent emissions.

11. The kit of claim 10, wherein the substance comprises an enzyme.

12. The kit of claim 10, further comprising a chemiluminescent enhancing agent which enhances the chemiluminescent emissions generated by the decomposition of the dioxetane.

13. The kit of claim 12, wherein the chemiluminescent enhancing agent is a quaternary onium polymer.

14. The kit of claim 12, further comprising an enhancement additive which further enhances the chemiluminescent emissions generated by the decomposition of the dioxetane.

15. A kit for detecting the presence of an analyte in a sample comprising:
the 1,2-dioxetane compound of claim 2; and
a substance which, in the presence of said dioxetane, causes said dioxetane to decompose and generate chemiluminescent emissions.

16. A method for detecting the presence and/or amount of an analyte in a sample, comprising:
adding the dioxetane compound of claim 1 to the sample, wherein the analyte is capable of removing the protecting group X from the dioxetane compound by non-enzymatic chemical or enzymatic means thereby causing the dioxetane compound to generate light;
incubating the sample; and
inspecting the sample for the presence of light;
wherein the presence of light indicates the presence of the analyte in the sample and wherein the amount of light indicates the amount of the analyte in the sample.

17. The method of claim 16, further comprising adding a chemiluminescent enhancement agent to the sample to enhance the light generated.

18. The method of claim 17, wherein the enhancement against is an quaternary onium polymer.

19. The method of claim 17, further comprising adding an enhancement additive to the sample to further enhance the light generated.

20. The method of claim 16, wherein the step of inspecting the sample comprises detecting light with a CCD camera.

21. The method of claim 16, wherein the analyte comprises an enzyme.

22. The method of claim 21, wherein the enzyme is complexed with a biological moiety.

23. A method for detecting the presence and/or amount of two or more analytes in a sample, comprising:
adding first and second chemiluminescent compounds to the sample, wherein the first chemiluminescent compound is the dioxetane compound of claim 1, and wherein one of the analytes is capable of removing the protecting group X from the first dioxetane compound by non-enzymatic chemical or enzymatic means thereby causing the first dioxetane compound to generate light of a first wavelength and wherein the other analyte causes the second chemiluminescent compound to decompose and generate light of a second wavelength different than the first wavelength;
incubating the sample; and
inspecting the sample for the presence of light;
wherein the presence of light of a particular wavelength indicates the presence of the corresponding analyte in the sample and wherein the amount of light of a particular wavelength indicates the amount of the corresponding analyte in the sample.

24. The method of claim 23, wherein the substituent Y in the first chemiluminescent compound is 3-pyridyl.

25. The method of claim 24, wherein the second chemiluminescent compound emits light in the blue portion of the visible spectrum upon decomposition.

26. The method of claim 25, wherein the second chemiluminescent compound emits light having a $\lambda_{max}$ of approximately 470 nm upon decomposition.

27. The compound of claim 3, wherein the heteroaryl group Y is 2-benzoxazolyl.

28. The compound of claim 3, wherein the heteroaryl group Y is 2-benzofuranyl.

29. The compound of claim 3, wherein the heteroaryl group Y is 2-benzothienyl.

* * * * *